(12) United States Patent
Kim et al.

(10) Patent No.: US 10,654,889 B2
(45) Date of Patent: May 19, 2020

(54) PEPTIDE HAVING ANTICANCER ACTIVITY, AND PHARMACEUTICAL COMPOSITION, HEALTH FUNCTIONAL FOOD COMPOSITION AND FUNCTIONAL COSMETIC COMPOSITION FOR PREVENTING AND TREATING CANCER COMPRISING THE SAME AS ACTIVE INGREDIENT

(71) Applicant: INDUSTRY-UNIVERSITY COOPERATION FOUNDATION HANYANG UNIVERSITY, Seoul (KR)

(72) Inventors: Chul Geun Kim, Seoul (KR); Chan Gil Kim, Chungcheongbuk-do (KR); Minyoung Kim, Incheon (KR); Hongnam Sim, Seoul (KR)

(73) Assignee: INDUSTRY-UNIVERSITY COOPERATION FOUNDATION HANYANG UNIVERSITY (KR)

( * ) Notice: Subject to any disclaimer, the term of this patent is extended or adjusted under 35 U.S.C. 154(b) by 0 days.

(21) Appl. No.: 16/329,139

(22) PCT Filed: Aug. 28, 2017

(86) PCT No.: PCT/KR2017/009366
§ 371 (c)(1),
(2) Date: Feb. 27, 2019

(87) PCT Pub. No.: WO2018/044012
PCT Pub. Date: Mar. 8, 2018

(65) Prior Publication Data
US 2019/0202860 A1     Jul. 4, 2019

(30) Foreign Application Priority Data
Aug. 30, 2016 (KR) .................... 10-2016-0111040

(51) Int. Cl.
| | |
|---|---|
| A61K 38/00 | (2006.01) |
| C07K 5/10 | (2006.01) |
| A61K 8/64 | (2006.01) |
| A23L 33/18 | (2016.01) |
| A61K 38/08 | (2019.01) |
| A61Q 19/00 | (2006.01) |
| C07K 7/06 | (2006.01) |
| C07K 7/64 | (2006.01) |
| A61K 38/06 | (2006.01) |
| A61K 38/07 | (2006.01) |
| A61P 35/00 | (2006.01) |
| C07K 7/08 | (2006.01) |
| C07K 14/00 | (2006.01) |

(52) U.S. Cl.
CPC ................ *C07K 5/10* (2013.01); *A23L 33/18* (2016.08); *A61K 8/64* (2013.01); *A61K 38/06* (2013.01); *A61K 38/07* (2013.01); *A61K 38/08* (2013.01); *A61P 35/00* (2018.01); *A61Q 19/00* (2013.01); *C07K 7/06* (2013.01); *C07K 7/08* (2013.01); *C07K 7/64* (2013.01); *C07K 14/001* (2013.01); *A23V 2002/00* (2013.01); *A61K 38/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 8,367,621 B2 | 2/2013 | Ruoslahti et al. | |
| 2013/0028899 A1 | 1/2013 | Sarkar et al. | |
| 2014/0113858 A1* | 4/2014 | Han ..................... | C07K 14/001 514/7.6 |

FOREIGN PATENT DOCUMENTS

| | | |
|---|---|---|
| WO | 98/36641 | 8/1998 |
| WO | 2009/033737 | 3/2009 |

OTHER PUBLICATIONS

Grant et al., "Antiproliferative small-molecule inhibitors of transcription factor LSF reveal oncogene addiction to LSF in hepatocellular carcinoma", PNAS, Mar. 20, 2012, vol. 109, No. 12, 4503-4508.
International Search report for PCT/KR2017/009366, dated Dec. 11, 2017, 20 pages.
Kang et al., "Identification and characterization of four novel peptide motifs that recognize distinct regions of the transcription factor CP2", FEBS Journal 272 (2005) 1265-1277.
Kim et al., "A DNA immunoprecipitation assay used in quantitative detection of in vitro DNA-protein complex binding", Analytical Biochemistry 441 (2013) 147-151.

* cited by examiner

Primary Examiner — Jeanette M Lieb
(74) Attorney, Agent, or Firm — Adsero IP

(57) ABSTRACT

The present invention relates to a peptide having anticancer activity, and a pharmaceutical composition, health functional food composition and functional cosmetic composition for preventing and treating cancer including the same as an active ingredient, and more particularly, to a peptide set forth in SEQ ID NO: 1, wherein the peptide binds to a transcription factor CP2c and has prophylactic and therapeutic activities against cancer, and a pharmaceutical composition, a health functional food composition and a functional cosmetic composition for preventing and treating cancer including the same as an active ingredient.
<SEQ ID NO: 1>
Tyr-Pro-Gln-Arg.

14 Claims, 24 Drawing Sheets
Specification includes a Sequence Listing.

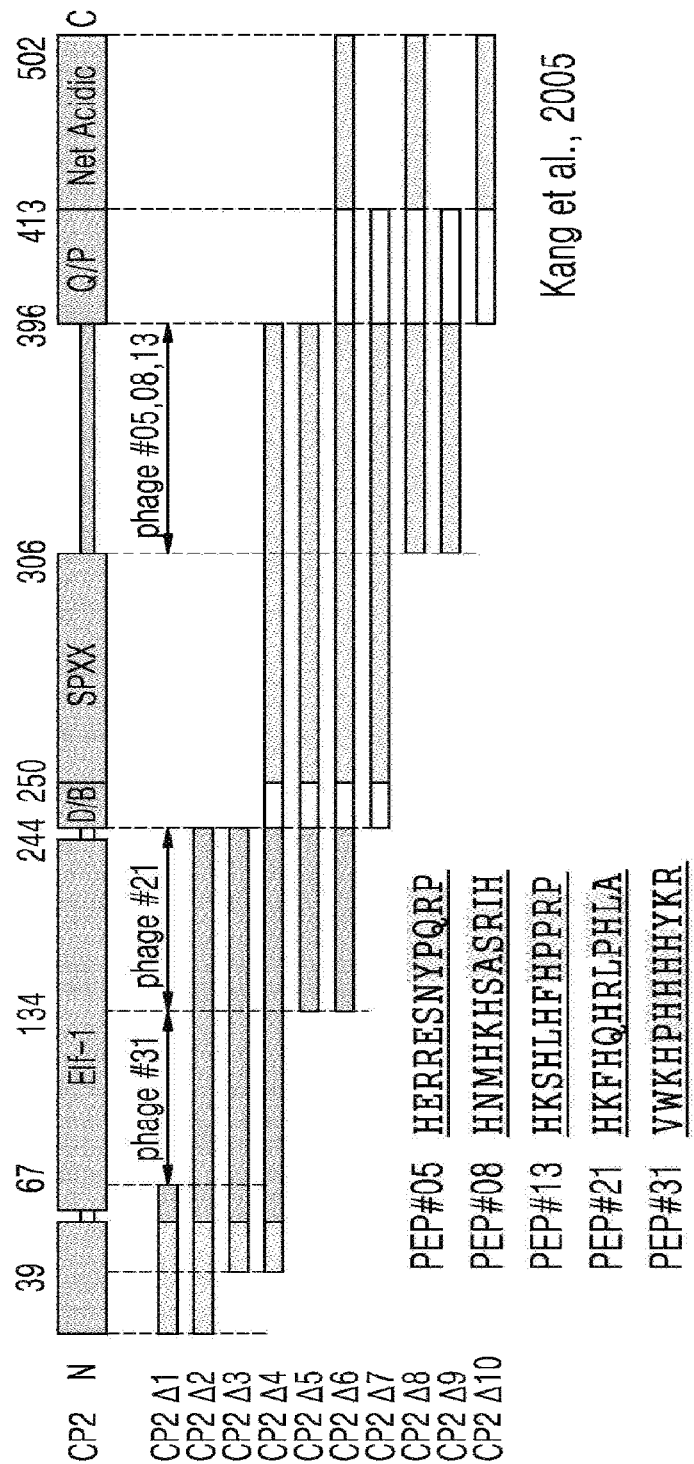

【Figure 2】
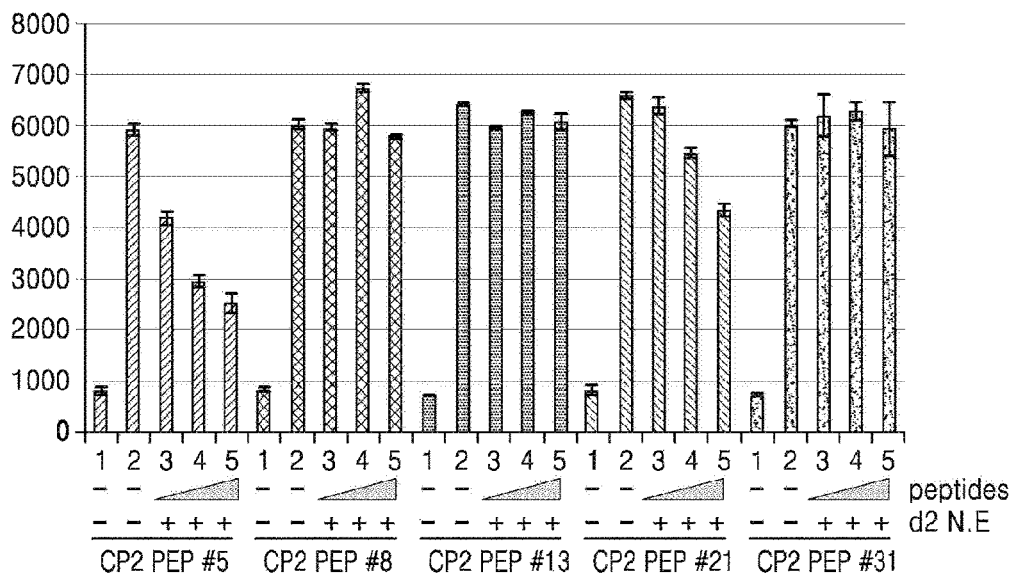
【Figure 3】
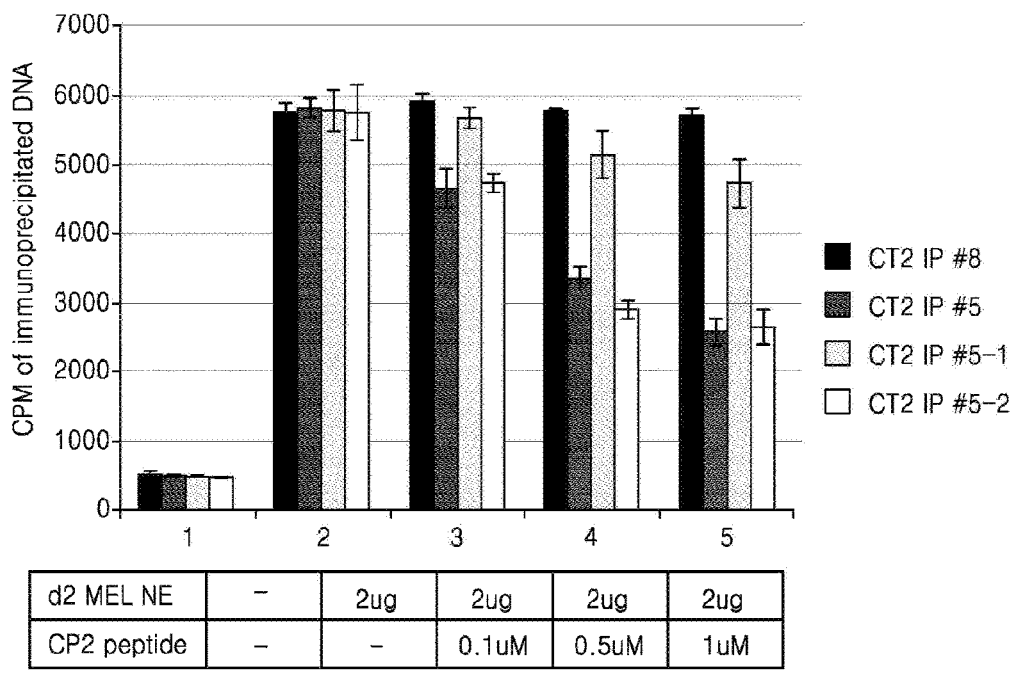

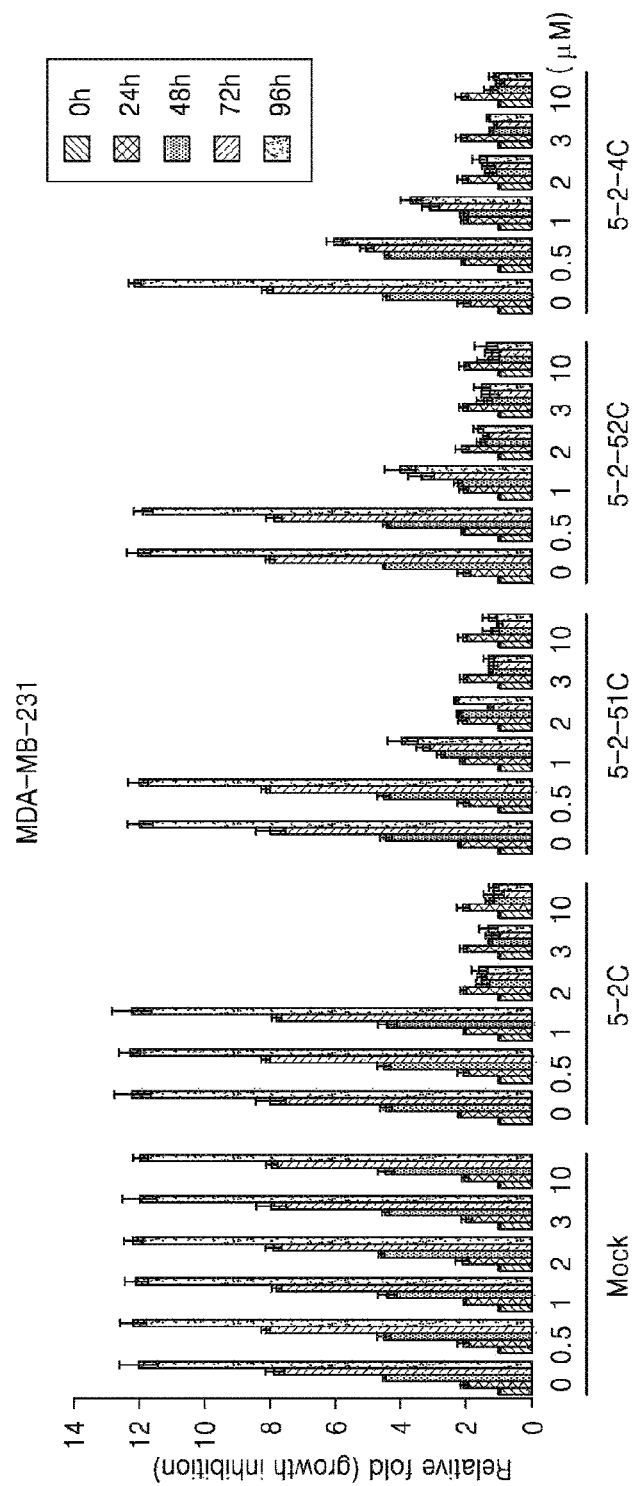
[Figure 4A]

[Figure 4B]
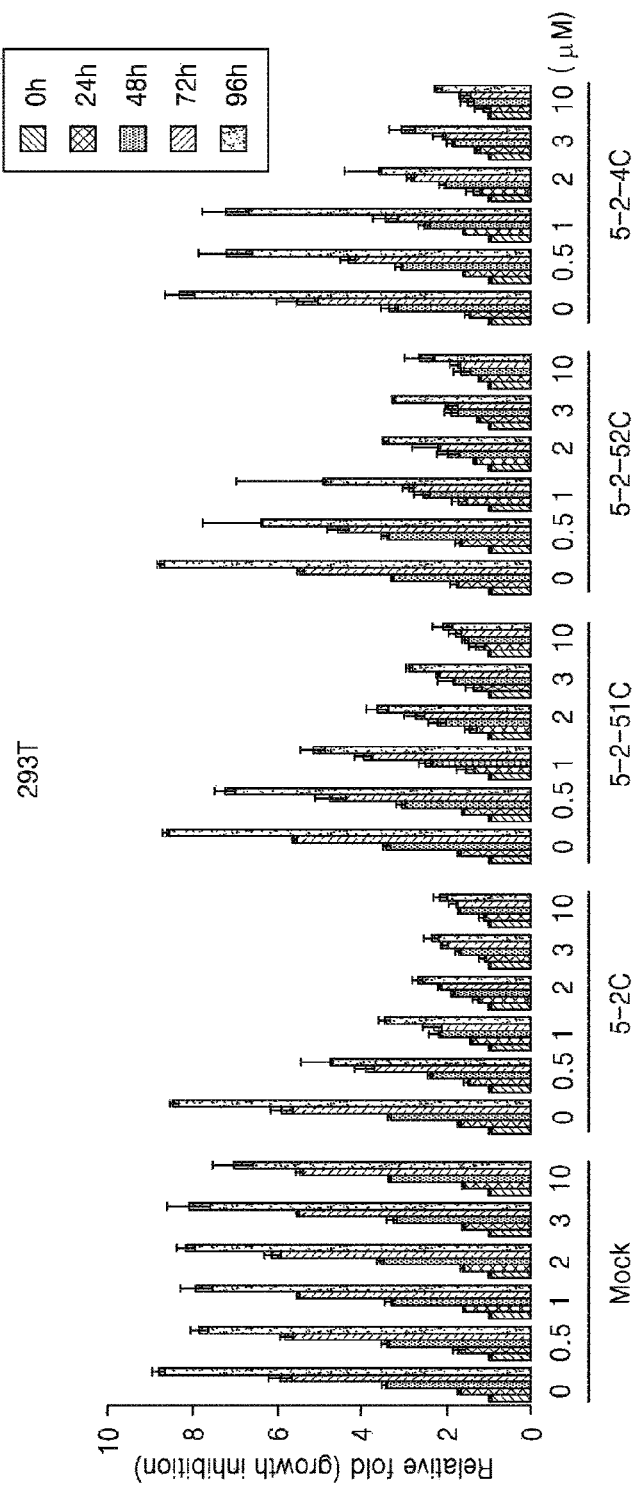

[Figure 5A]
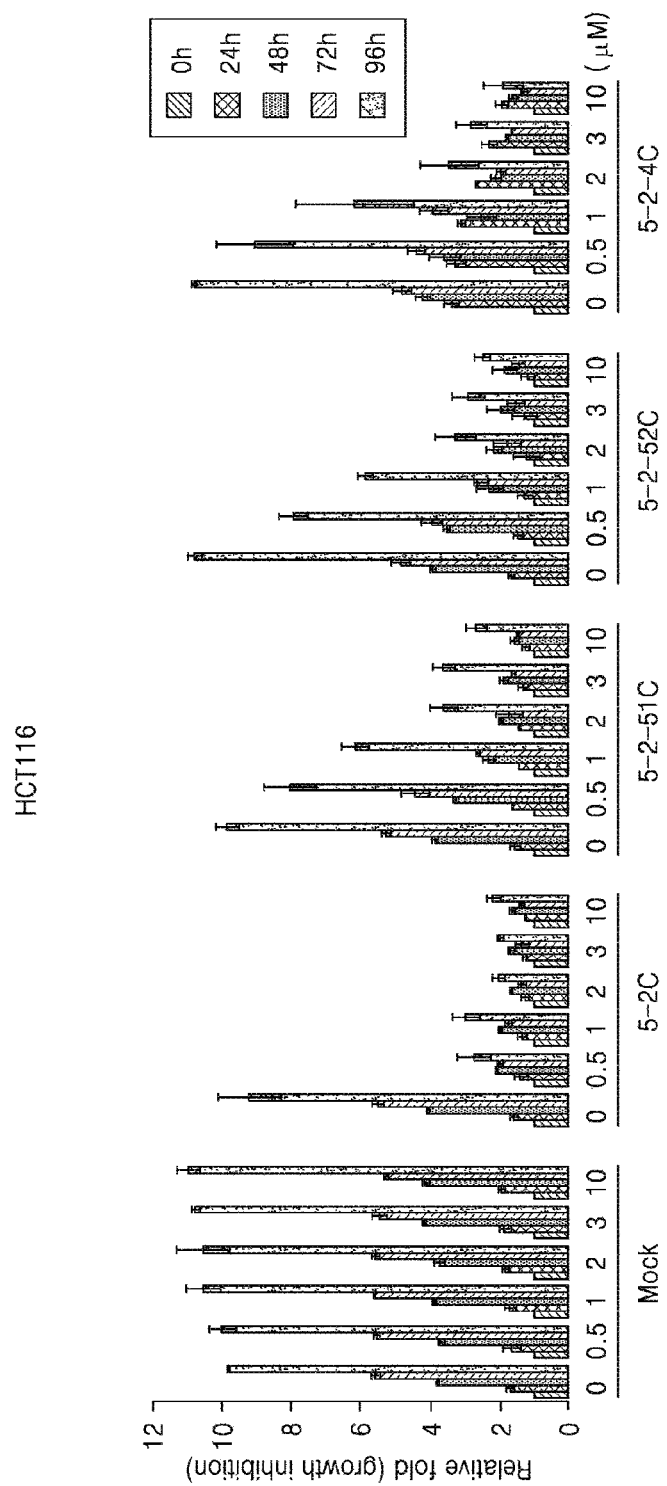

[Figure 5B]
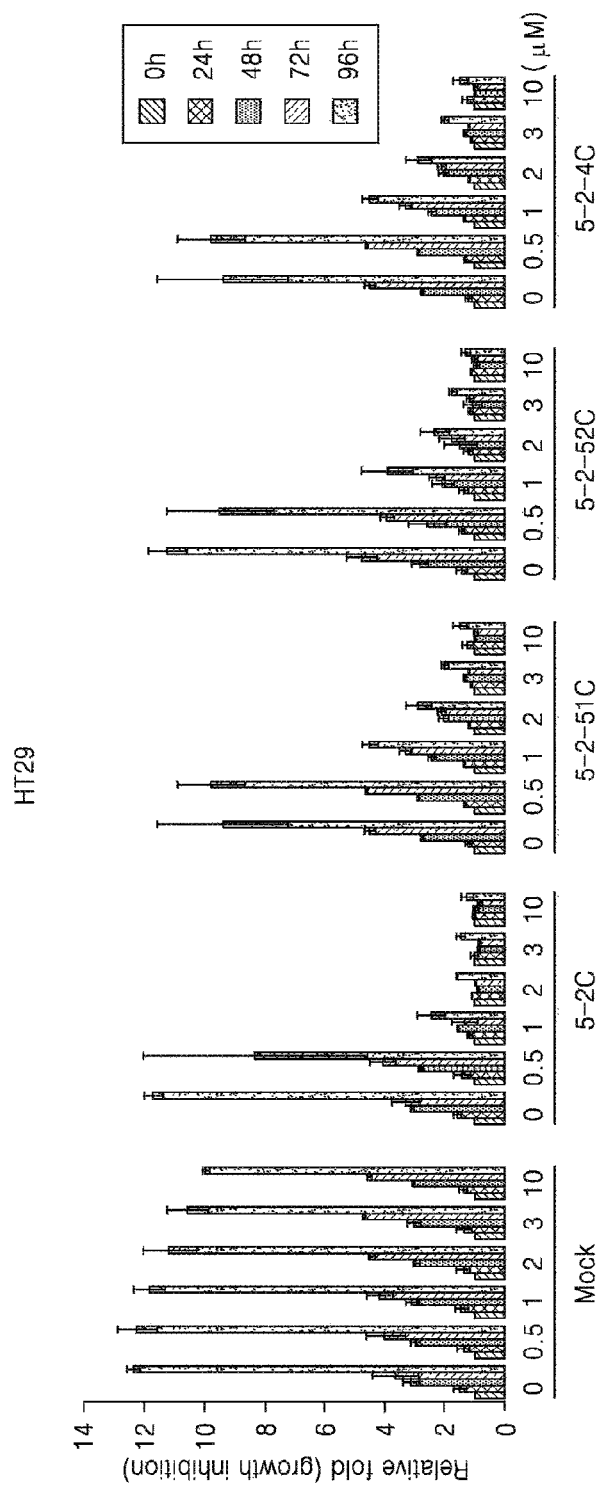

【Figure 6A】
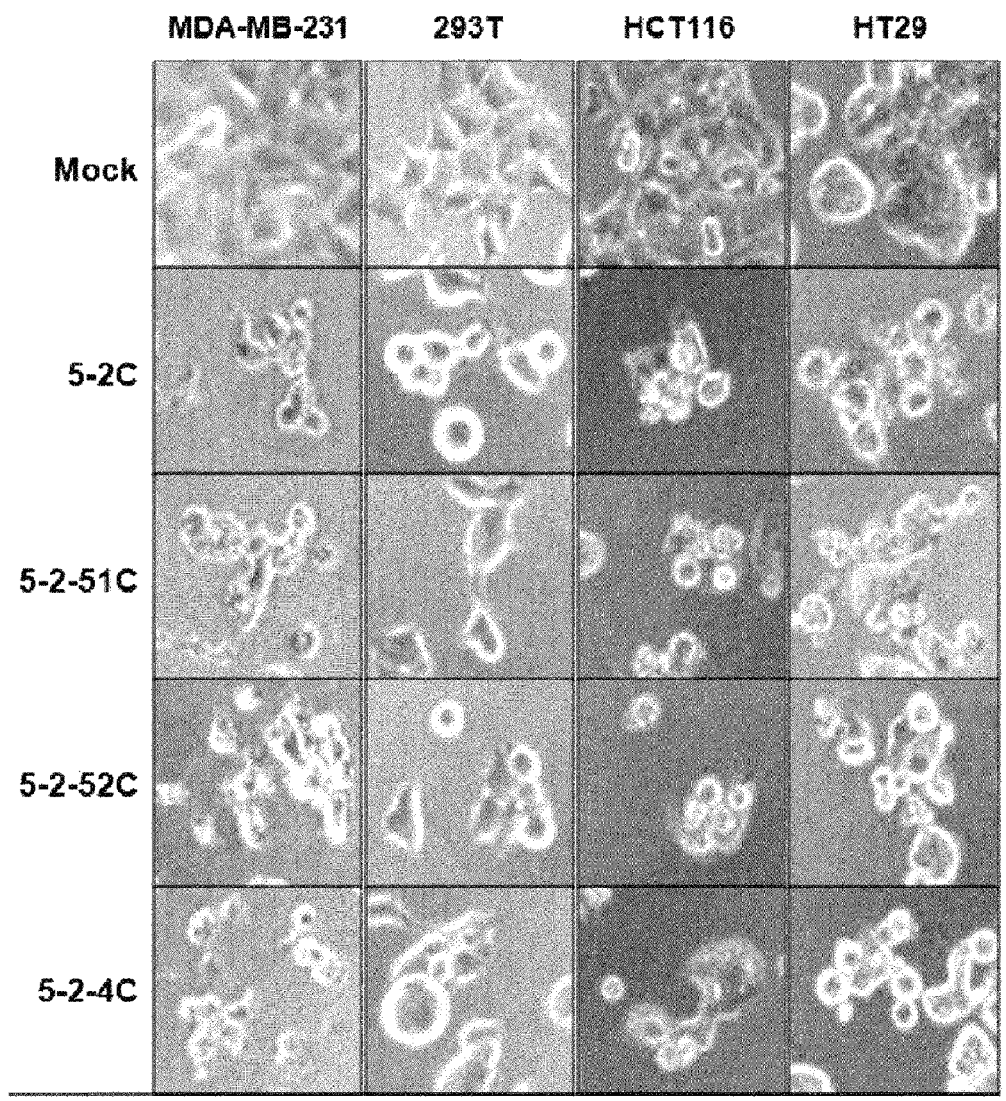

【Figure 6B】
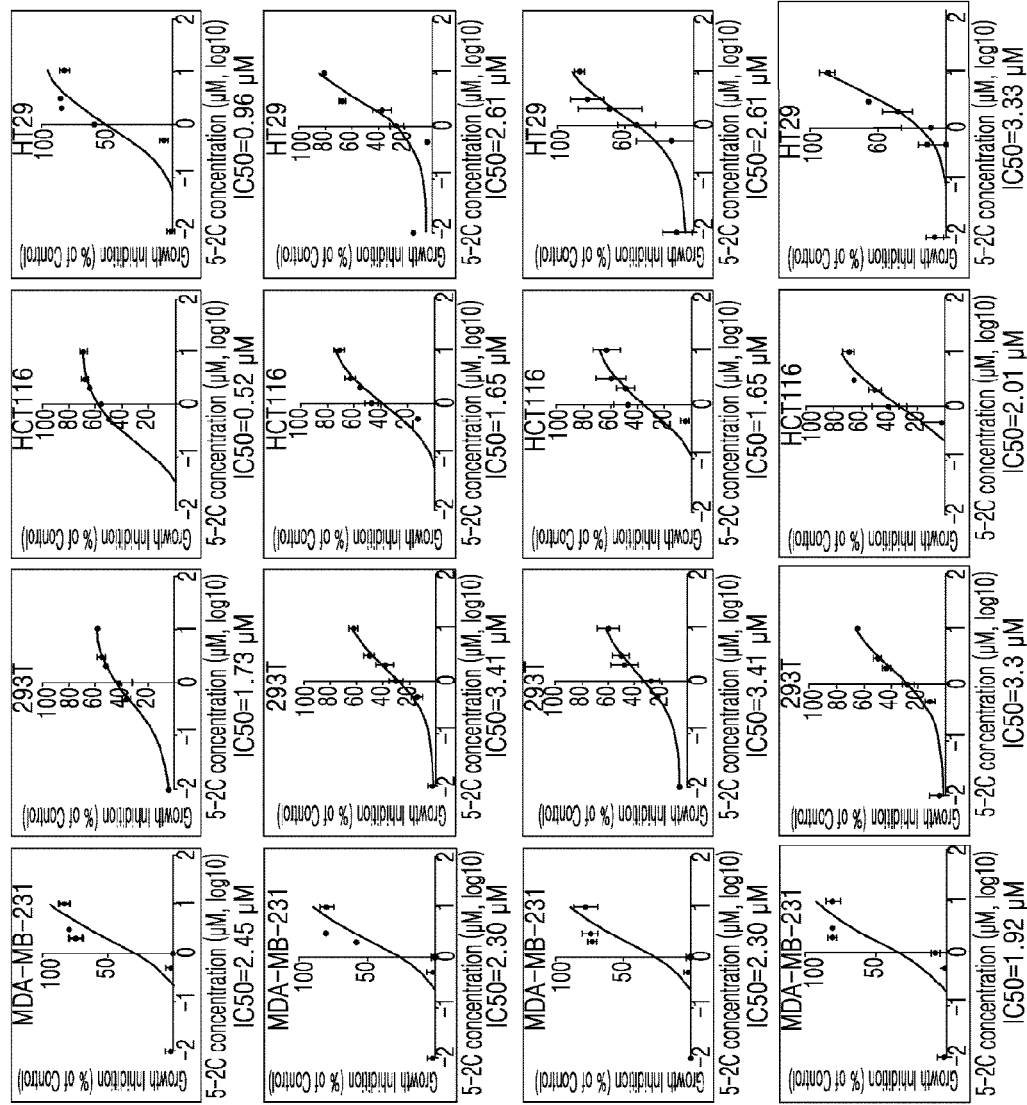

[Figure 6C]
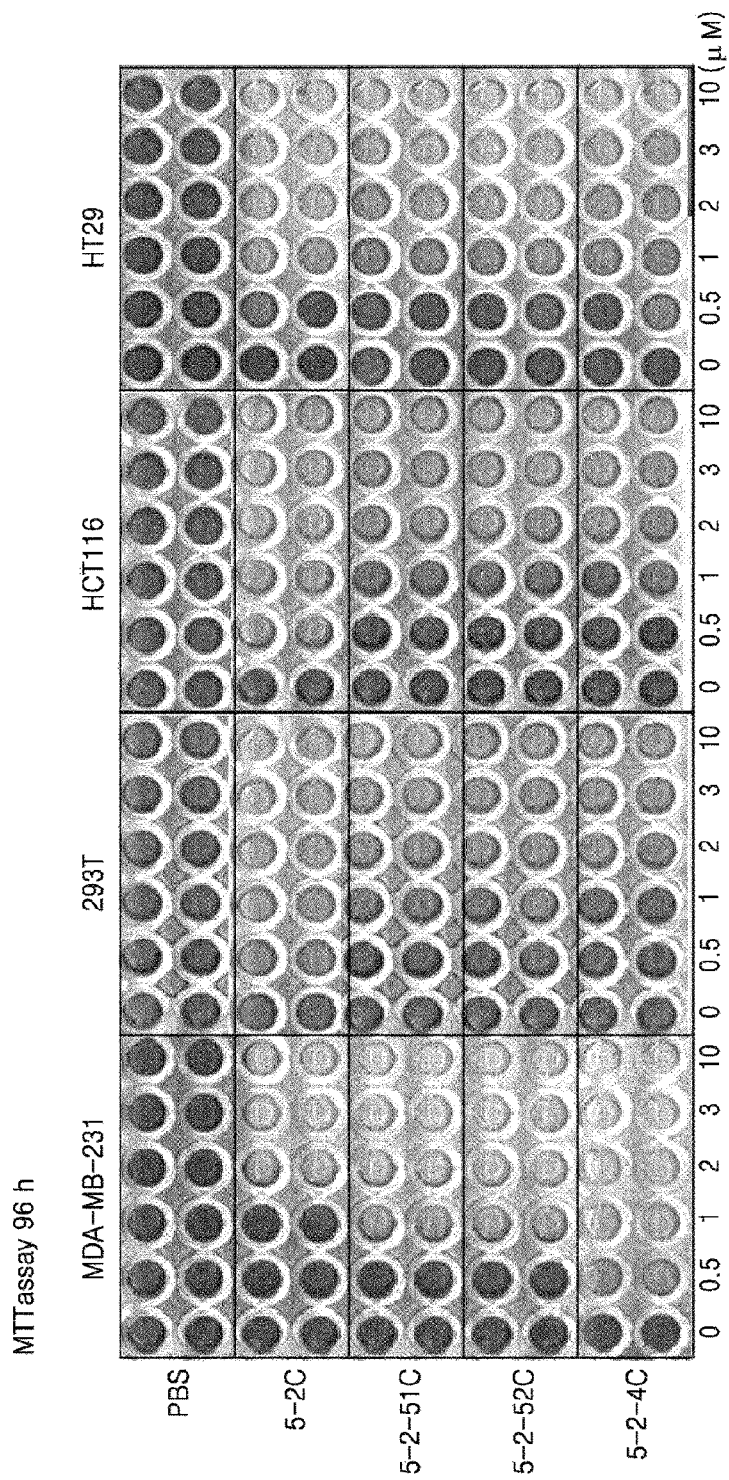

[Figure 7A]
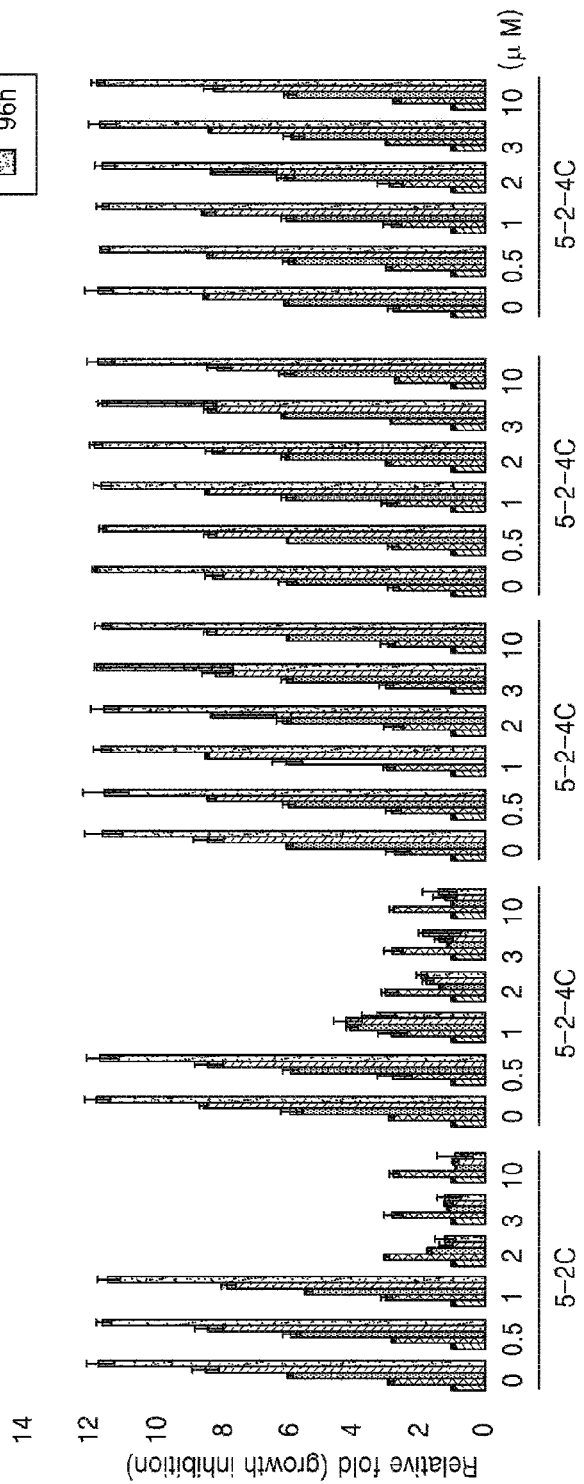

【Figure 7B】
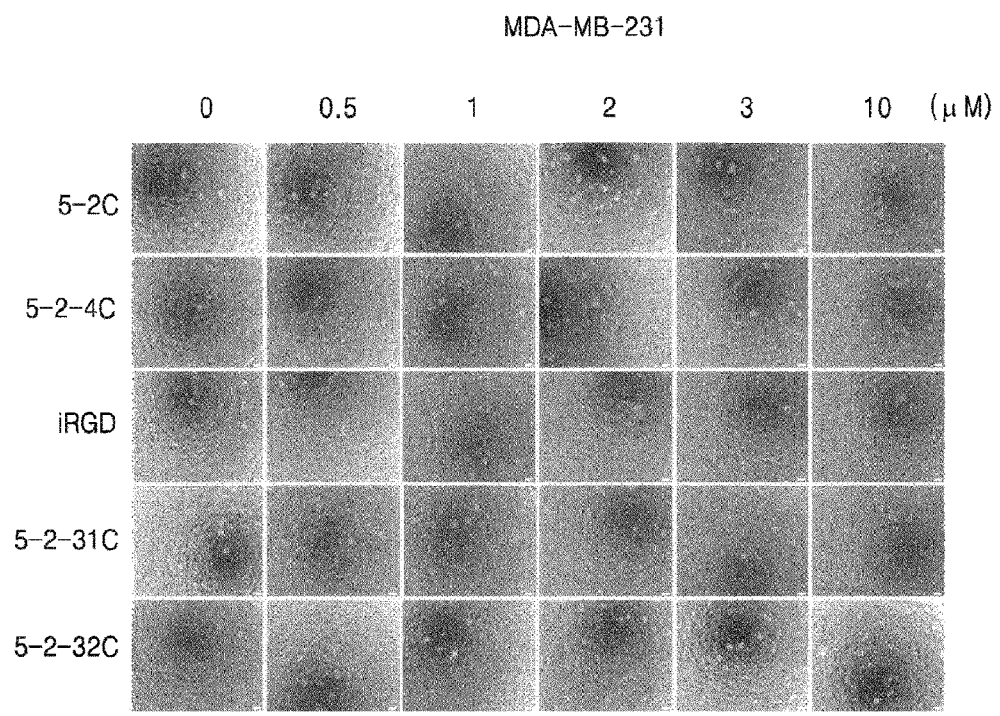

【Figure 7C】
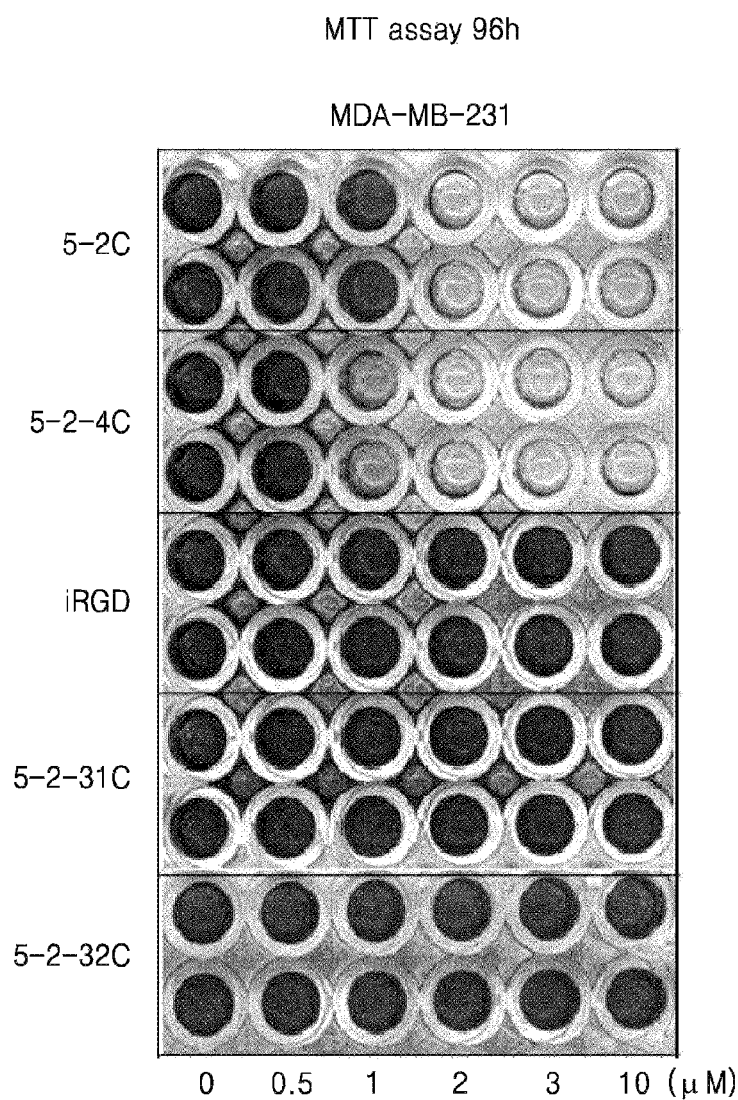

【Figure 7D】
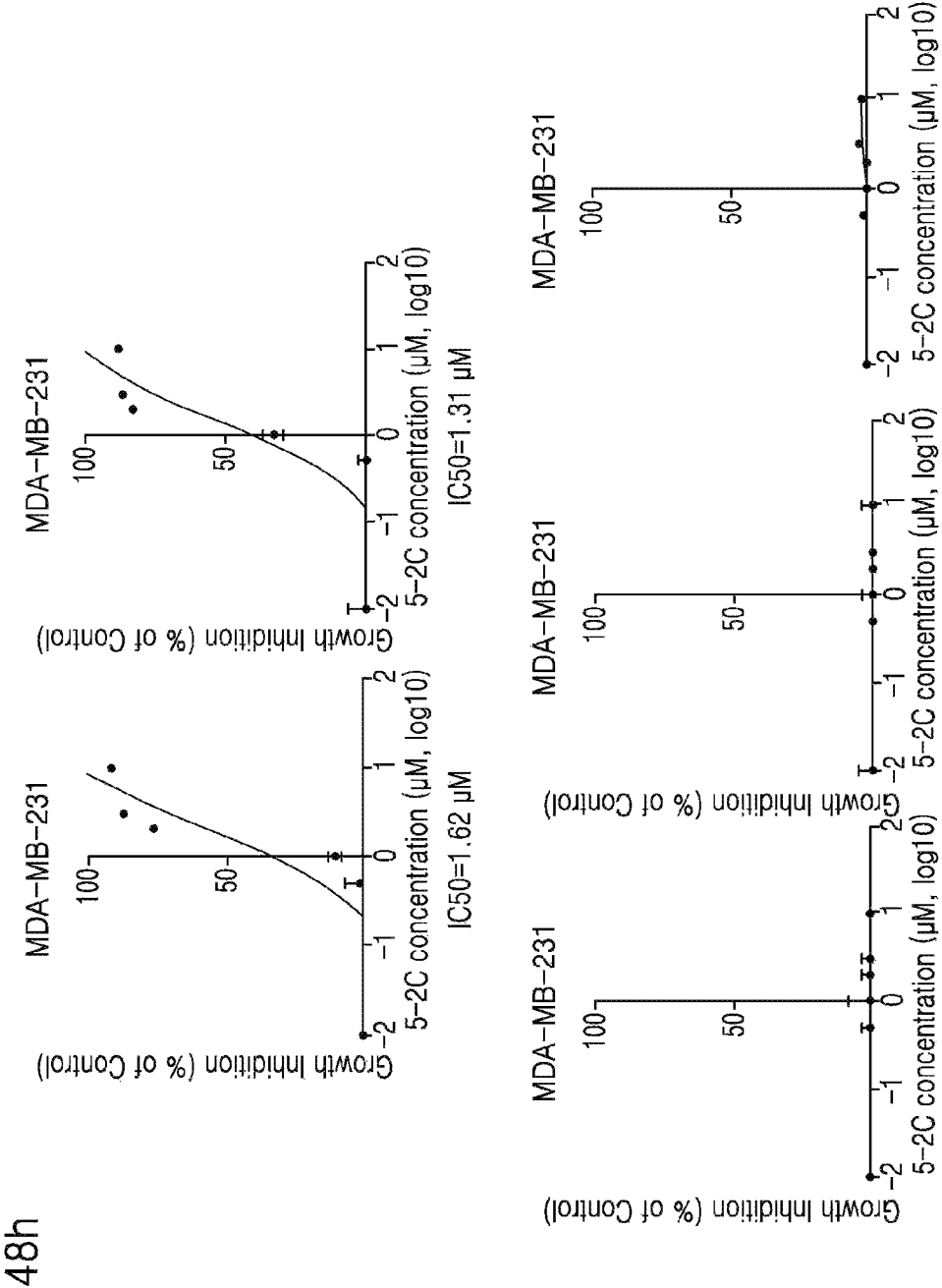

[Figure 8A]
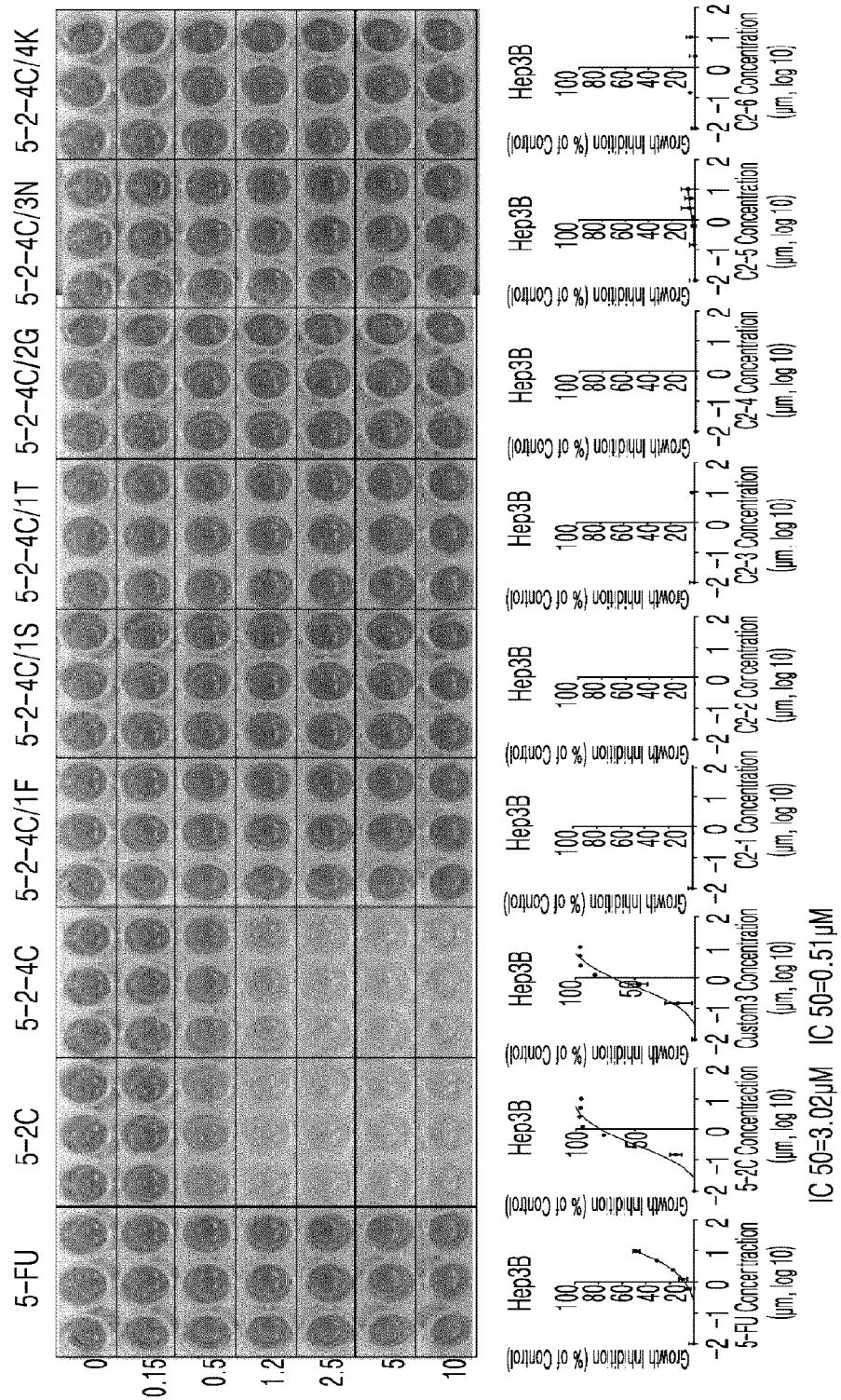

【Figure 8B】
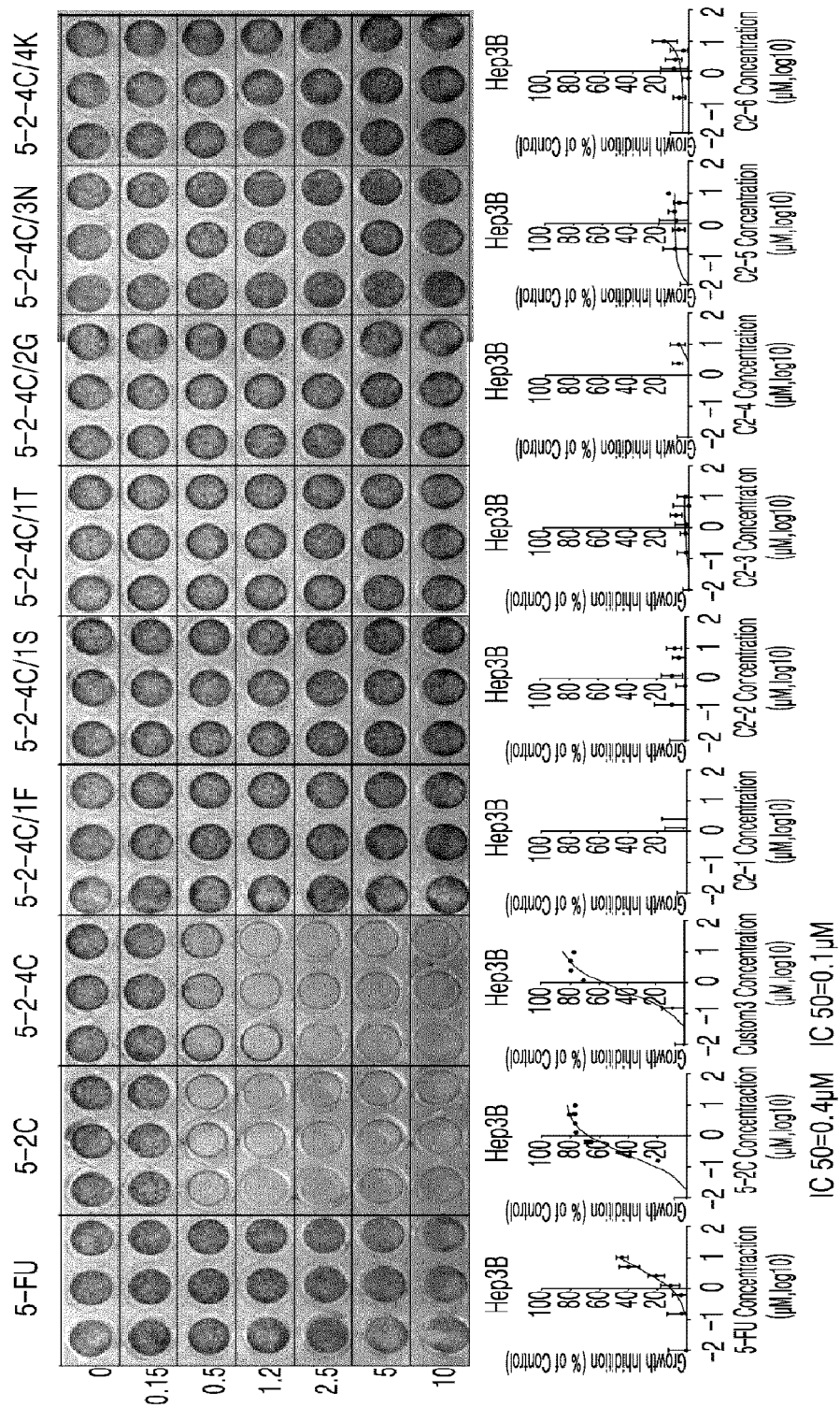

【Figure 8C】
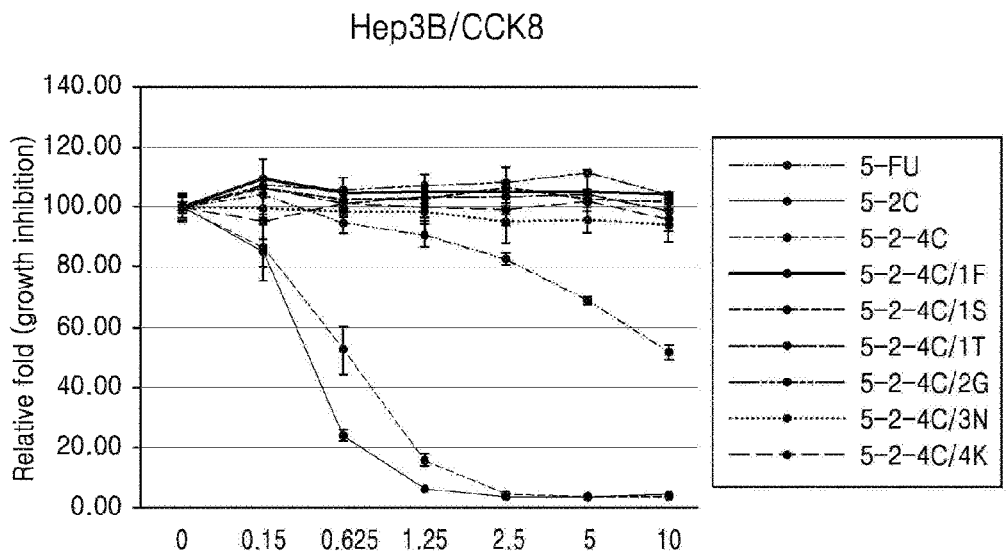
【Figure 8D】
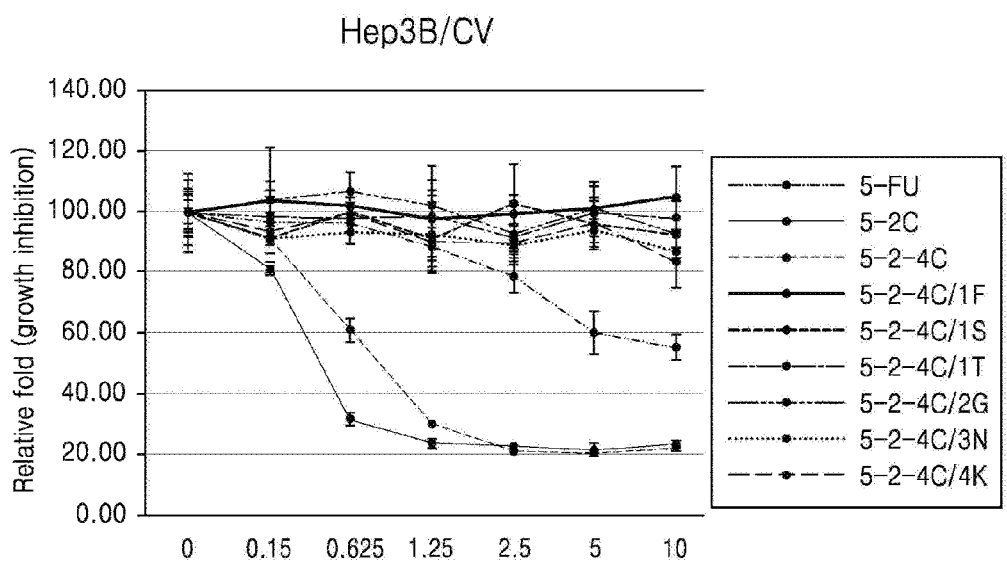

【Figure 9】
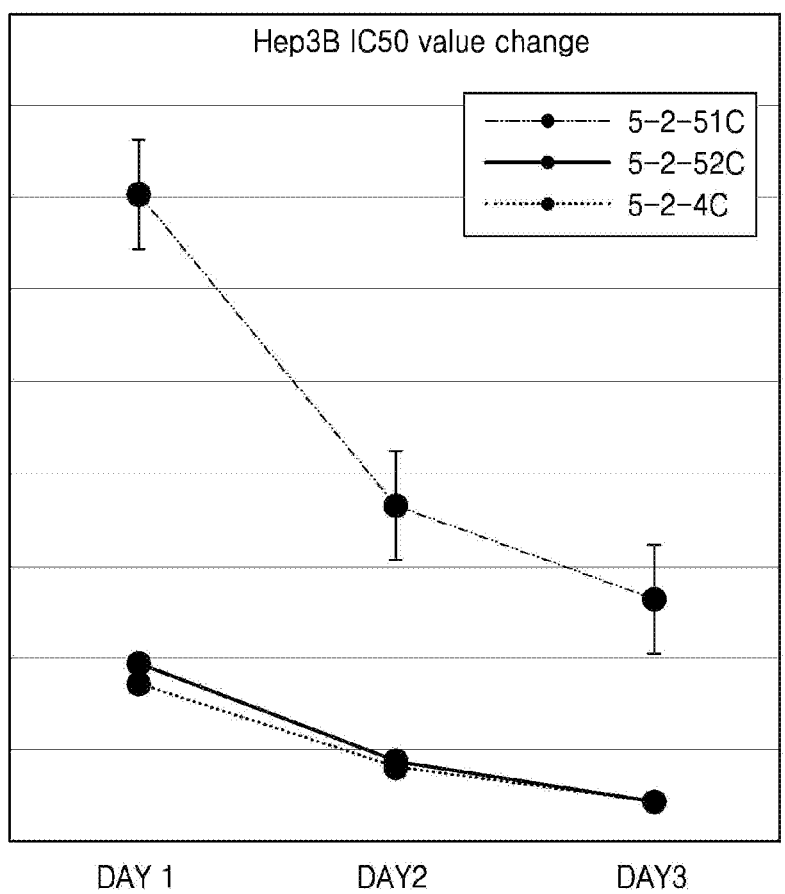

[Figure 10A]
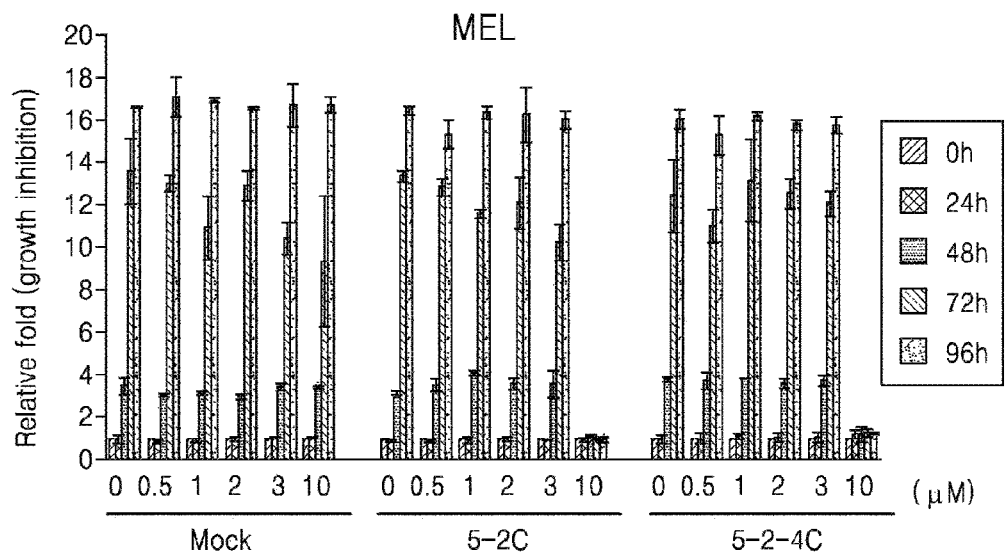
[Figure 10B]
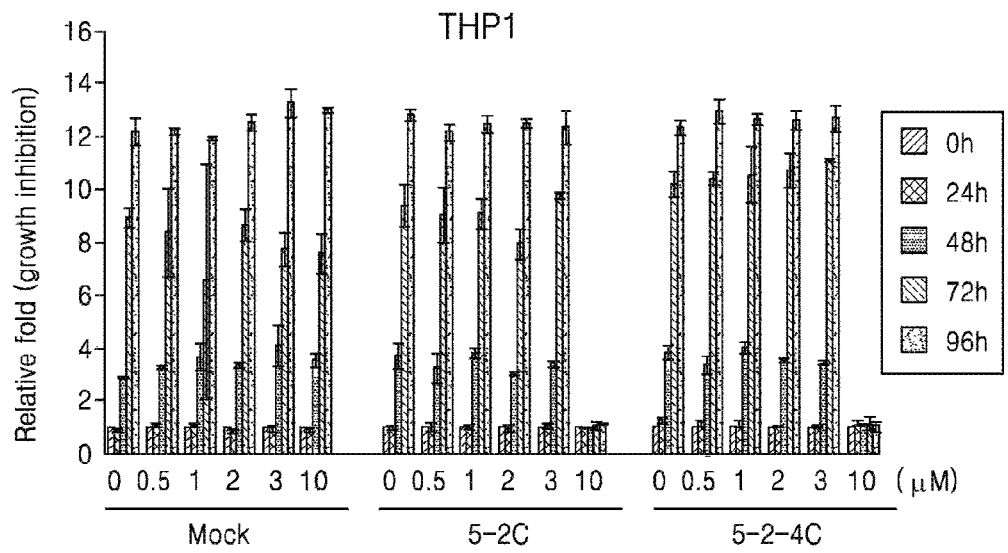

【Figure 11A】
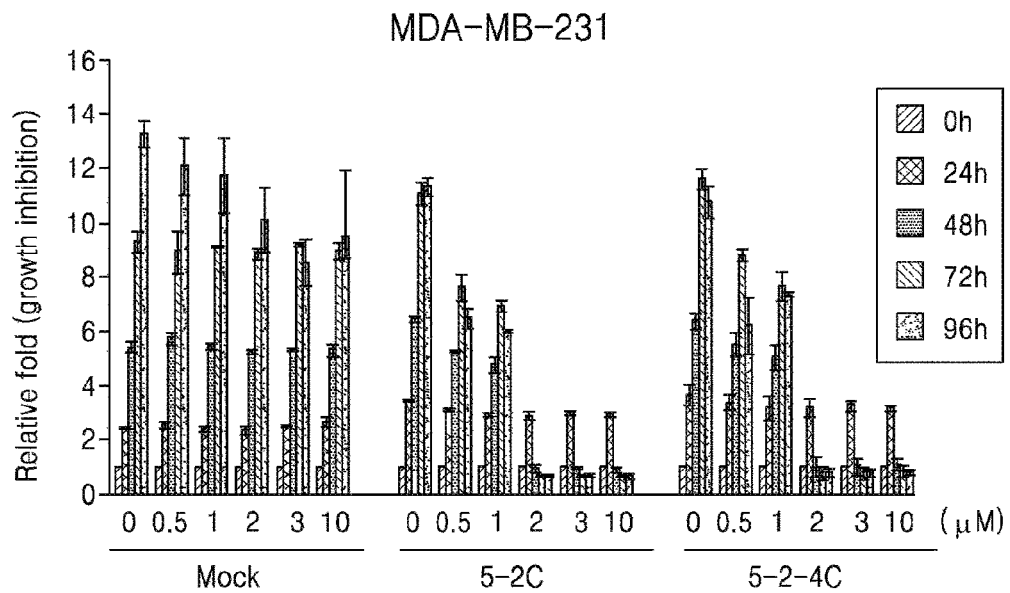
【Figure 11B】
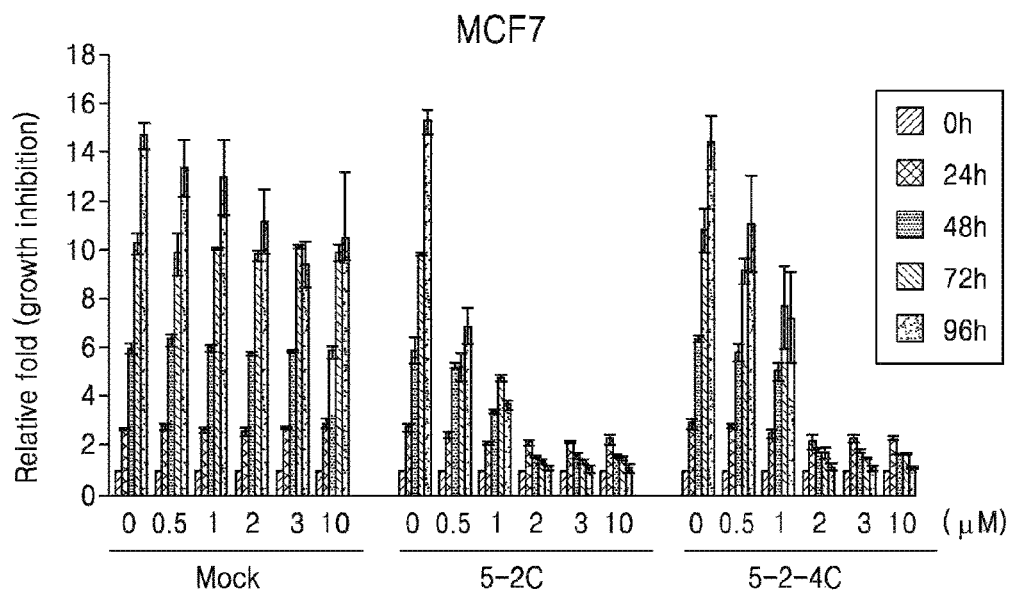

【Figure 12A】
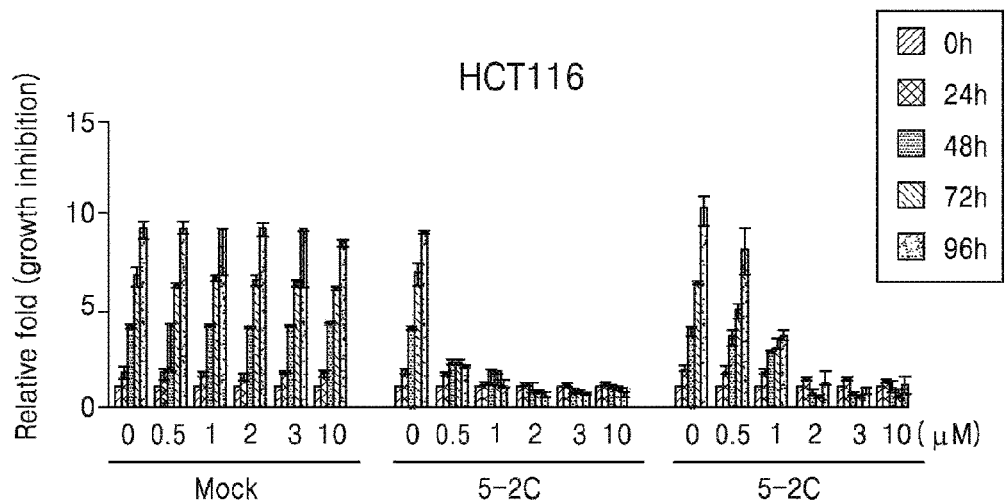
【Figure 12B】
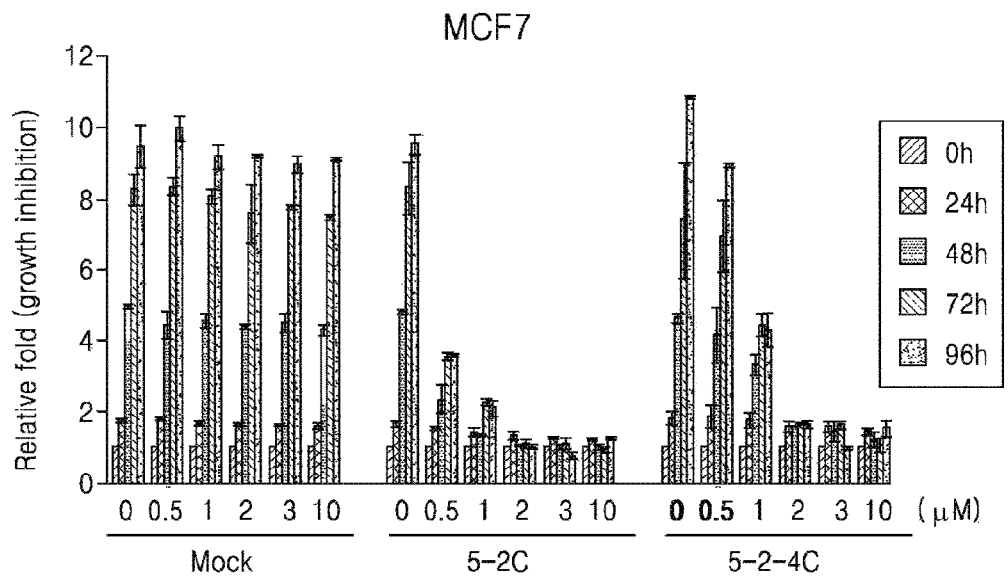

【Figure 13A】
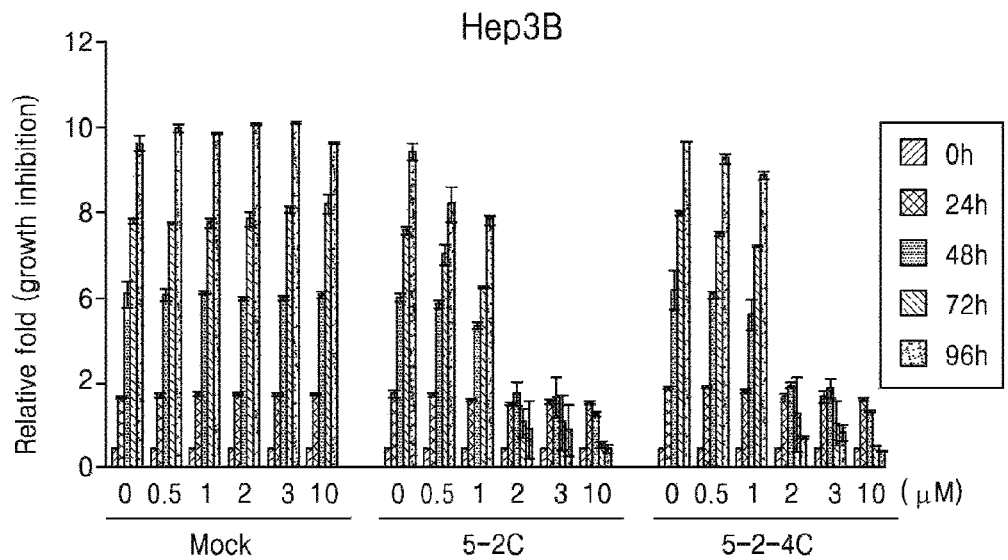
【Figure 13B】
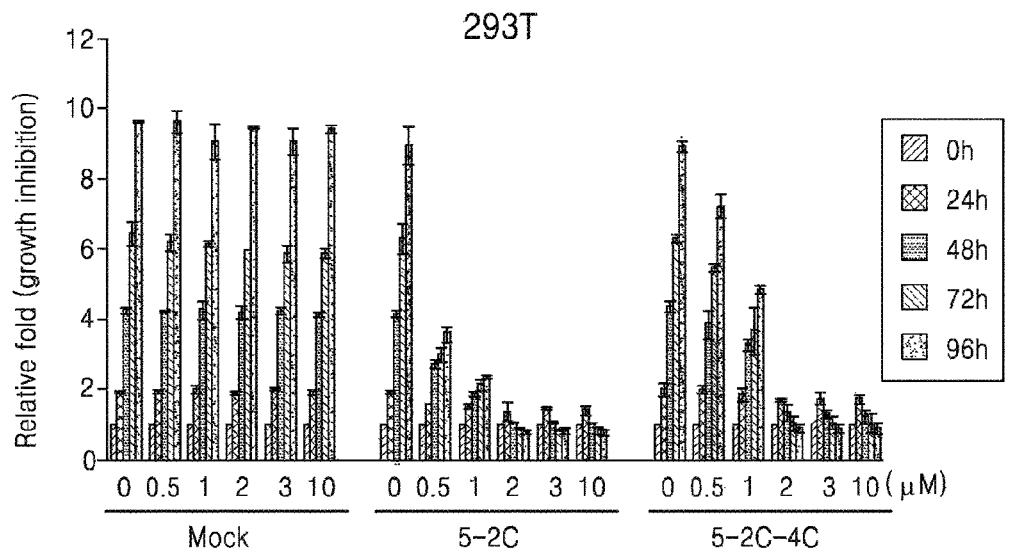

【Figure 14】
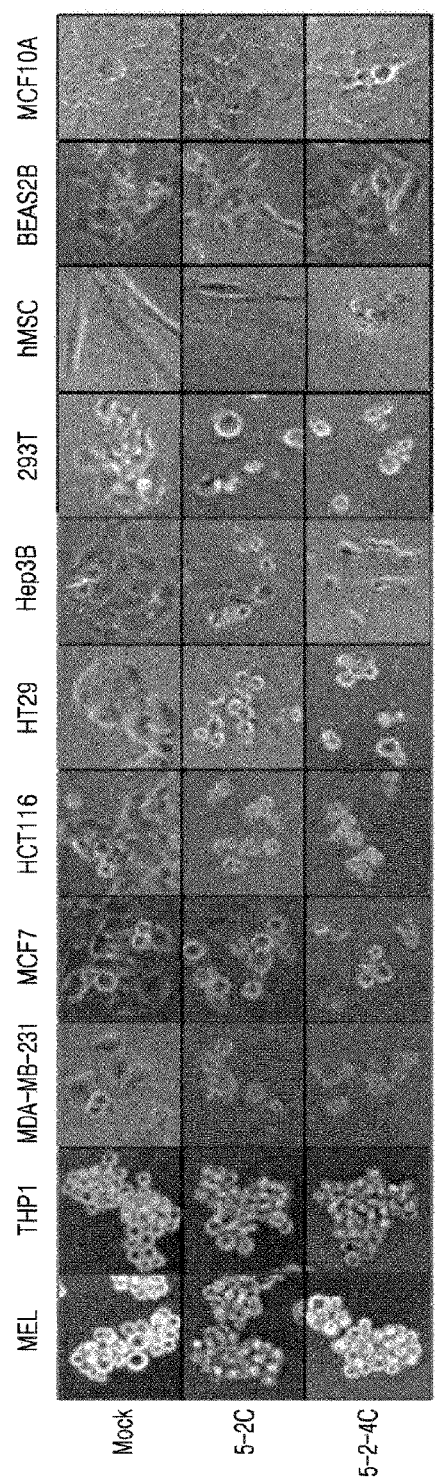

[Figure 15]
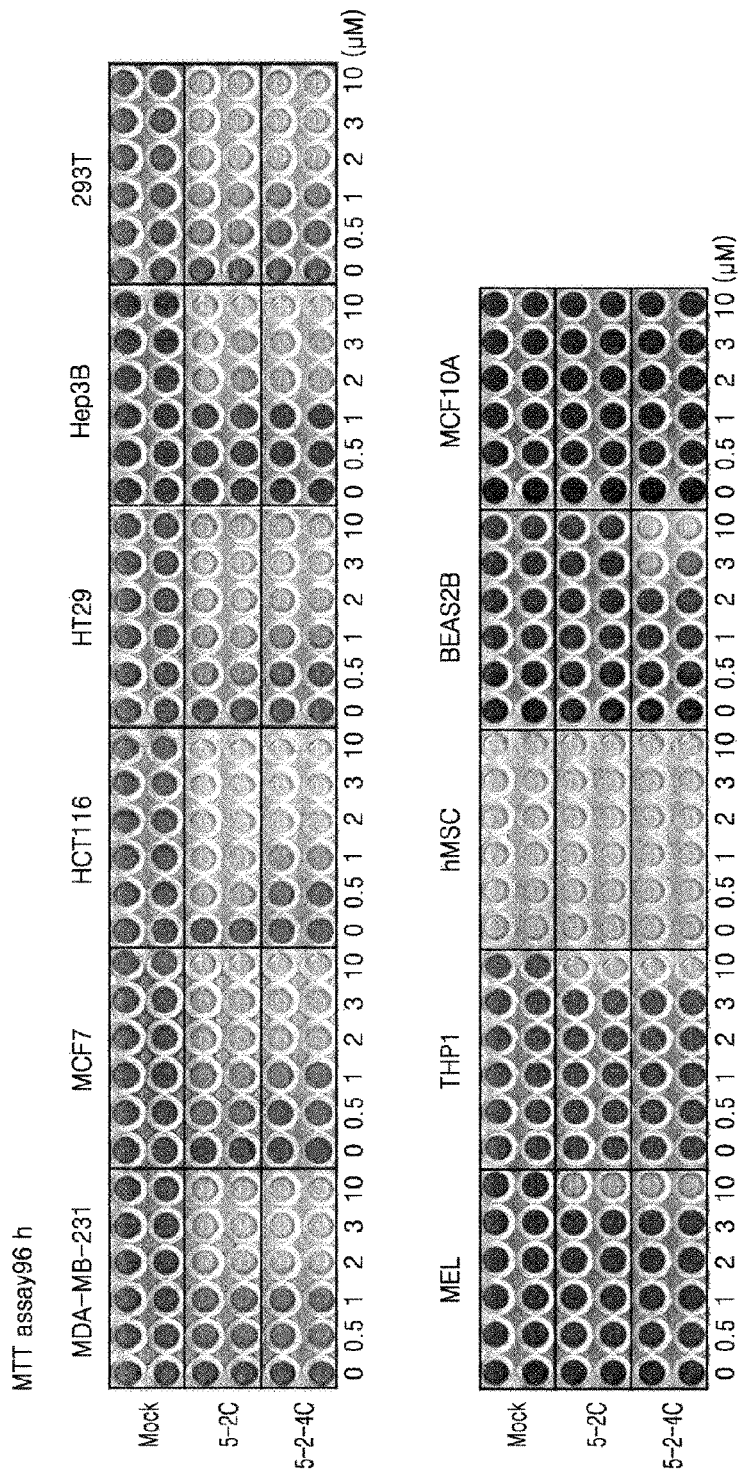

【Figure 16】
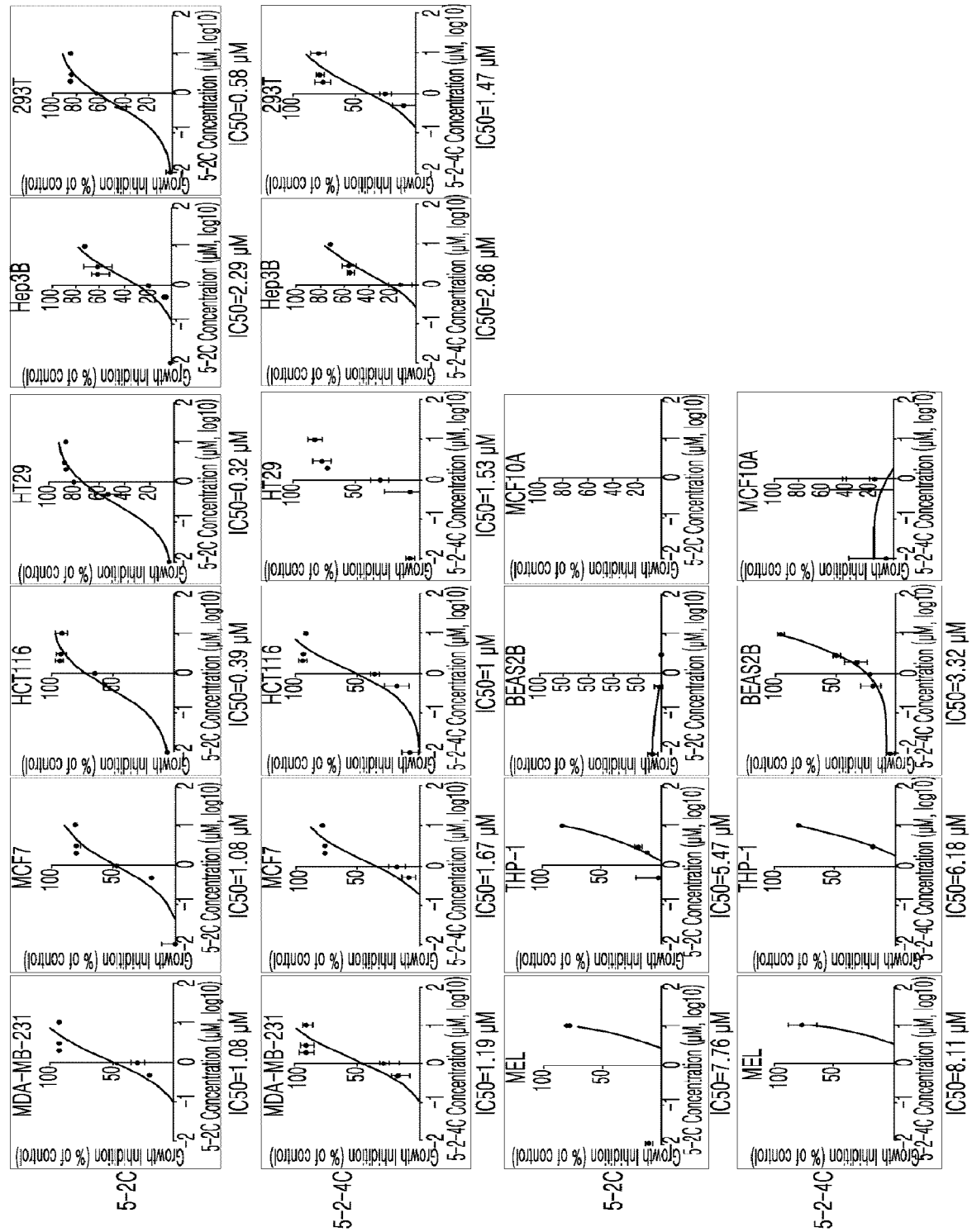

PEPTIDE HAVING ANTICANCER ACTIVITY, AND PHARMACEUTICAL COMPOSITION, HEALTH FUNCTIONAL FOOD COMPOSITION AND FUNCTIONAL COSMETIC COMPOSITION FOR PREVENTING AND TREATING CANCER COMPRISING THE SAME AS ACTIVE INGREDIENT

CROSS-REFERENCE TO RELATED APPLICATION

This application claims priority to and is a 35 U.S.C. § 371 national phase application of PCT/KR2017/009366 (WO2018/044012), filed on Aug. 28, 2017 entitled "PEPTIDE HAVING ANTICANCER ACTIVITY, AND CANCER PREVENTING AND TREATING PHARMACEUTICAL COMPOSITION, FUNCTIONAL HEALTH FOOD COMPOSITION AND FUNCTIONAL COSMETIC COMPOSITION CONTAINING SAME AS ACTIVE INGREDIENT", which application claims priority to and the benefit of Korean Patent Application No. 10-2016-0111040, filed Aug. 30, 2016, 2016; the disclosures of which are incorporated herein by reference in their entirety.

SEQUENCE STATEMENT Incorporated by reference herein in its entirety is the Sequence Listing entitled "sequence_US_ST25_0338_137PCT_US," created Feb. 22, 2019, size of 2 kilobytes.

TECHNICAL FIELD

The present invention relates to a peptide having anticancer activity, and a pharmaceutical composition, health functional food composition and functional cosmetic composition for preventing and treating cancer including the same as an active ingredient.

BACKGROUND ART

Various drugs including natural products, protein or peptide anticancer drugs, and chemically synthetic anticancer drugs, have been developed and used so far. However, most of these drugs cause serious side effects affecting normal cells in vivo, and may not work depending on the type of carcinoma. In general cases, the drugs may also not work depending on patients suffering from the same type of carcinoma. Under such circumstances, numerous worldwide studies have been conducted to develop, as novel anticancer drugs used to solve these problems, anticancer drugs capable of selectively removing only cancer cells without affecting normal cells in vivo and further removing all types of cancer cells as well.

A transcription factor CP2c (also known as the terms CP2, Tfcp2, LSF, LBP1, UBP1, etc.) is widely expressed in various mammals, and the activity of CP2c is elaborately regulated as the cells transition from the resting phase (G0) to the DNA replication phase (S), the process of which is essential in allowing the cells to pass through the G1/S transition phase. The regulation of CP2c activity is mostly achieved through post-translational modifications, and a low level of the CP2c activity is maintained constantly. However, because the CP2c is overexpressed in tumor cells, it plays a critical role in carcinogenesis.

In this regard, a research group at Boston University (USA) reported Factor Quinolinone Inhibitor 1 (FQI1) as a compound for inhibiting the cellular activity of CP2c in a liver cancer cell line, identified FQI1 and derivatives thereof using a chemical library screening method, and found that the FQI1 and derivatives thereof are successful in inhibiting only the cancer cells without exerting any influence on normal cells in cell and mouse xenograft models (Grant et al., Antiproliferative small-molecule inhibitors of transcription factor LSF reveal oncogene addiction to LSF in hepatocellular carcinoma, Proc. Natl. Acad. Sci. 2012; 109(12): 4503-4508).

Further, the present inventors also have reported four novel peptide motifs (HXPR, PHL, ASR, and PXHXH) recognizing a specific region of CP2c (Kang et al., Identification and characterization of four novel peptide motifs that recognize distinct regions of the transcription factor CP2, FEBS Journal 2005; 272:1265-1277), and proposed that the CP2c recognizes specific binding motifs of a target protein and interacts with the protein to regulate various cellular activities. In their follow-up study, the present inventors have screened peptides inhibiting the binding of CP2c to DNA by means of an in vitro analysis method based on a DNA immunoprecipitation assay that is useful for analyzing DNA-protein interactions with very specific and high sensitivity, and thus found that Peptide 5 composed of 12 amino acids inhibits CP2c-DNA binding in a concentration-dependent manner (Kim et al., A DNA immunoprecipitation assay used in quantitative detection of in vitro DNA-protein complex binding, Analytical Biochemistry. 2013; 441: 147-151).

DISCLOSURE

Technical Problem

The present invention has been made based on the results of previous studies conducted by the present inventors and is directed to providing a peptide for more effective inhibition of the activity of CP2c known as a key transcription factor in various carcinomas, and a pharmaceutical composition, a health functional food composition and a functional cosmetic composition for preventing and treating cancer containing the peptide as an active ingredient.

Technical Solution

To solve the above problems, the present invention provides a peptide set forth in SEQ ID NO: 1, wherein the peptide binds to a transcription factor CP2c and has prophylactic and therapeutic activities against cancer.

<SEQ ID NO: 1>
Tyr-Pro-Gln-Arg

According to one exemplary embodiment of the present invention, acetyl and amide groups may be bound to N-terminal Tyr and C-terminal Arg of the peptide set forth in SEQ ID NO: 1, respectively.

According to another exemplary embodiment of the present invention, a peptide set forth in the following SEQ ID NO: 2 may be bound to the C-terminal Arg of the peptide set forth in SEQ ID NO: 1.

<SEQ ID NO: 2>
Cys-Arg-Gly-Asp-Lys-Gly-Pro-Asp-Cys

According to still another exemplary embodiment of the present invention, when the peptide set forth in SEQ ID NO: 2 is bound to the C-terminal Arg of the peptide set forth in SEQ ID NO: 1, acetyl and amide groups may be bound to the N-terminal Tyr of the peptide set forth in SEQ ID NO: 1 and C-terminal Cys of the peptide set forth in SEQ ID NO: 2, respectively.

According to yet another exemplary embodiment of the present invention, the peptide set forth in SEQ ID NO: 2 and a peptide set forth in the following SEQ ID NO: 3 may be bound to the C-terminal Arg and the N-terminal Tyr of the peptide set forth in SEQ ID NO: 1, respectively, and fluorescein isothiocyanate (FITC) may be bound to N-terminal Lys of the peptide set forth in SEQ ID NO: 3.

<SEQ ID NO: 3>
Lys-Cys-Lys-Gly-Gly-Ser-Gly-Gly-Ser (provided that each of Lys 1 and 3 residues of the sequence is 6-aminohexanoic acid.)

According to yet another exemplary embodiment of the present invention, when the peptide set forth in SEQ ID NO: 2 is bound to the C-terminal Arg of the peptide set forth in SEQ ID NO: 1 and the peptide set forth in SEQ ID NO: 3 is bound to the N-terminal Tyr of the peptide set forth in SEQ ID NO: 1, an amide group may be bound to the C-terminal Cys of the peptide set forth in SEQ ID NO: 2.

According to yet another exemplary embodiment of the present invention, a peptide set forth in the following SEQ ID NO: 4 may be bound to the C-terminal Arg of the peptide set forth in SEQ ID NO: 1.

<SEQ ID NO: 4>
Arg-Gly-Asp

According to yet another exemplary embodiment of the present invention, when the peptide set forth in SEQ ID NO: 4 is bound to the C-terminal Arg of the peptide set forth in SEQ ID NO: 1, acetyl and amide groups may be bound to the N-terminal Tyr of the peptide set forth in SEQ ID NO: 1 and C-terminal Cys of the peptide set forth in SEQ ID NO: 4, respectively.

According to yet another exemplary embodiment of the present invention, when the peptide set forth in SEQ ID NO: 4 is bound to the C-terminal Arg of the peptide set forth in SEQ ID NO: 1, a cyclic peptide may be formed via a direct peptide bond between the amino group of the N-terminal Tyr of the peptide set forth in SEQ ID NO: 1 and the carboxyl group of the C-terminal Cys of the peptide set forth in SEQ ID NO: 4.

According to yet another exemplary embodiment of the present invention, a peptide set forth in the following SEQ ID NO: 5 may be bound to the N-terminal Tyr of the peptide set forth in SEQ ID NO: 1.

<SEQ ID NO: 5>
Lys-Ile-Lys-Lys-Val-Lys-Lys-Lys-Gly-Arg-Lys-Gly-
Ser-Lys-Ile-Lys-Lys-Val-Lys-Lys-Lys-Gly-Arg-Lys-
Gly-Gly

According to yet another exemplary embodiment of the present invention, when the peptide set forth in SEQ ID NO: 5 is bound to the N-terminal Tyr of the peptide set forth in SEQ ID NO: 1, acetyl and amide groups may be bound to N-terminal Lys of the peptide set forth in SEQ ID NO: 5 and the C-terminal Arg of the peptide set forth in SEQ ID NO: 1, respectively.

According to yet another exemplary embodiment of the present invention, the peptide set forth in SEQ ID NO: 2 may be bound to the C-terminal Arg of the peptide set forth in SEQ ID NO: 1 and biotin-labeled Lys may be bound to ε-$NH_2$ of the C-terminal Cys of the peptide set forth in SEQ ID NO: 2.

According to yet another exemplary embodiment of the present invention, when the peptide set forth in SEQ ID NO: 2 is bound to the C-terminal Arg of the peptide set forth in SEQ ID NO: 1 and the biotin-labeled Lys is bound to the ε-$NH_2$ of the C-terminal Cys of the peptide set forth in SEQ ID NO: 2, acetyl and amide groups may be bound to the N-terminal Tyr of the peptide set forth in SEQ ID NO: 1 and the biotin-labeled C-terminal Lys bound to the ε-$NH_2$ of the C-terminal Cys of the peptide set forth in SEQ ID NO: 2, respectively.

Also, the present invention provides a pharmaceutical composition for preventing and treating cancer including the peptide as an active ingredient.

In addition, the present invention provides a health functional food composition for preventing and treating cancer including the peptide as an active ingredient.

Further, the present invention provides a functional cosmetic composition including the peptide as an active ingredient.

Advantageous Effects

When cancer cells are treated with the peptide and the pharmaceutical composition including the same according to the present invention, the highly stable peptide and the pharmaceutical composition can penetrate cell membranes with very high efficiency, and thus can specifically bind to CP2c and inhibit the ability of CP2c to bind to DNA. Therefore, the peptide or the pharmaceutical composition of the present invention can inhibit the activity of CP2c to impede CP2c-mediated cancer cell-specific transcriptional activity, and thus can be effective in specifically treating cancer cells. In addition, the peptide or the pharmaceutical composition of the present invention can be used to prevent cancer and used as a health food additive for prevention of cancer, and can also be used as a functional cosmetic composition.

DESCRIPTION OF DRAWINGS

FIG. 1 is a diagram schematically showing a full-length amino acid sequence of CP2c composed of a total of 6 regions, and sequences of various CP2c mutants in which the N- and C-termini of the CP2c sequence are deleted.

FIG. 2 is a graph illustrating the binding affinities of DNA-CP2c complexes measured by performing a DNA immunoprecipitation (DIP) assay for five CP2c-bound peptides (Peptide 5, Peptide 8, Peptide 13, Peptide 21, and Peptide 31).

FIG. 3 is a graph illustrating the binding affinities of DNA-CP2c complexes by performing a DIP assay for Peptide 5, Peptide 8, Peptide 5-1, and Peptide 5-2.

FIGS. 4A and 4B are diagrams graphically showing growth inhibition and apoptosis-inducing effects of the untreated control and Peptides 5-2C, 5-2-51C, 5-2-52C and 5-2-4C on a breast cancer cell line (4A) and an embryonic kidney cell line (4B).

FIGS. 5A and 5B are diagrams graphically showing growth inhibition and apoptosis-inducing effects of the untreated control, and the Peptides 5-2C, 5-2-51C, 5-2-52C and 5-2-4C on two colon cancer cell lines (HCT116 and HT29).

FIGS. 6A to 6C includes an image (6A) of cells, a graph (6B) for cell growth inhibition by means of an MTT assay for calculating $10_{50}$ values, and an image (6C) of 96-well plates for MTT assay at the elapsed time of 96 hours after an embryonic kidney cell line (293T), a breast cancer cell line (MDA-MB-231), and colon cancer cell lines (HCT116 and HT29) are treated with the untreated control, and the Peptides 5-2C, 5-2-51C, 5-2-52C and 5-2-4C for 48 hours FIG. 7A is a diagram showing growth inhibition and apoptosis-inducing effects of the Peptides 5-2C, 5-2-4C, iRGD, 5-2-31C and 5-2-32C on a breast cancer cell line (MDA-MB-231), FIG. 7B is an image of cells, FIG. 7C is an image of 96-well plates for MTT assay at the elapsed time of 96 hours, and FIG. 7D is a diagram showing a graph for cell growth inhibition by means of an MTT assay for calculating $IC_{50}$ values.

FIGS. 8A and 8B are diagrams showing respective images of the 96-well plates for MTT assay stained with a cell counting kit (CCK) and Crystal Violet (CV) at the elapsed time of 96 hours, and FIGS. 8C and 8D are diagrams graphically showing growth inhibition and apoptosis-inducing effects of the respective peptides at different concentrations.

FIG. 9 is a graph illustrating daily changes in $IC_{50}$ values as observed for 3 days after a Hep3B liver cancer cell line is treated once with the Peptides 5-2-51C, 5-2-52C and 5-2-4C.

FIGS. 10A and 10B, FIGS. 11A and 11B, FIGS. 12A and 12B, and FIGS. 13A and 13B are diagrams graphically showing cell growth inhibition and apoptosis-inducing effects of the untreated control, a 5-2C peptide-treated group, and a 5-2-4C-treated group on leukemia cells; breast cancer cells; colon cancer cells, and liver cancer cells and kidney-derived cells at different concentrations, respectively.

FIG. 14 is a diagram showing images of cells after 48 hours of treatment of various cells with the peptides in the untreated control, a 5-2C peptide-treated group, and a 5-2-4C-treated group has elapsed.

FIG. 15 is a diagram showing images of well plates for MTT assay after 96 hours of treatment of various cells with the peptides in the untreated control, the 5-2C peptide-treated group, and the 5-2-4C-treated group has elapsed.

FIG. 16 is a graph illustrating $IC_{50}$ values after 96 hours of treatment of various cells with the peptides in the 5-2C peptide-treated group and the 5-2-4C-treated group has elapsed.

BEST MODE

Hereinafter, the present invention will be described in further detail.

To solve the above problems, the present invention provides a peptide set forth in SEQ ID NO: 1, wherein the peptide binds to a transcription factor CP2c and has therapeutic activity against cancer.

<SEQ ID NO: 1>
Tyr-Pro-Gln-Arg

The peptide of SEQ ID NO: 1 composed of four amino acids (hereinafter also referred to as 'Peptide 5-2-4') interacts with a CP2c protein to regulate the activity of the protein, as can be specifically seen from the Examples section below. Because CP2c is a protein that is specifically overexpressed in tumor cells, this activity regulation eventually leads to anticancer effects.

As described above, the present inventors have found that Peptide 5 composed of 12 amino acids inhibits the CP2c-DNA binding in a concentration-dependent manner. However, as can be seen from the results of the following Examples, such Peptide 5 composed of 12 amino acids induces cell growth inhibition and apoptosis even in normal control cell lines. Therefore, in the follow-up studies, the present inventors also have reported that Peptide 5-2 composed of 6 amino acids from Peptide 5 (having a sequence composed of the last six amino acids of Peptide 5) does not substantially affect growth inhibition and induction of apoptosis in normal control cell lines (Korean Patent Application No. 10-2015-0045480, unpublished).

Therefore, the present invention is intended to analyze a peptide with the minimum size composed of amino acids essential for anticancer effects in Peptide 5-2 composed of the six amino acids. As a result, it was found that the peptide set forth in SEQ ID NO: 1, which is composed of four amino acids, is essential for the anticancer effects.

Peptide 5-2-4 according to the present invention may be modified to have various functionalities. For example, modified peptides to be listed below may also be provided.

First, to enhance the stability of the peptide set forth in SEQ ID NO: 1, acetyl and amide groups may be bound to N-terminal Tyr and C-terminal Arg of the peptide, respectively (hereinafter also referred to as 'Peptide 5-2-4A').

Next, to enhance the cell penetrability of the peptide set forth in SEQ ID NO: 1, preferably, an iRGD peptide sequence (CRGDKGPDC) binding to a neuropilin 1 receptor may also be bound to C-terminal Arg of the peptide (hereinafter also referred to as 'Peptide 5-2-4B'). Likewise, acetyl and amide groups may also be bound to N-terminal Tyr and C-terminal Cys of the Peptide 5-2-4B, respectively (hereinafter also referred to as 'Peptide 5-2-4C').

To enhance the cell penetrability of the peptide set forth in SEQ ID NO: 1, an RGD peptide sequence (RGD) binding to integrin αv and a β3/β5 dimer may also be bound to the C-terminal Arg of the peptide (hereinafter also referred to as 'Peptide 5-2-4R'). Likewise, acetyl and amide groups may also be bound to N-terminal Tyr and C-terminal Cys of the Peptide 5-2-4R, respectively (hereinafter also referred to as 'Peptide 5-2-4RC'). Preferably, to enhance stability of the Peptide 5-2-4R peptide, formation of a peptide bond between an amino group and a carboxyl group of the N-terminal Tyr and the C-terminal Cys may also be induced to form a cyclic peptide (hereinafter also referred to as 'Peptide c (5-2-4R)').

To easily track the intracellular migration path and biodistribution of the Peptide 5-2-4 or 5-2-4C by means of fluorescence/confocal microscopy and bio-imaging methods, a FITC fluorescent substance-containing compound (FITC-(6-aminohexanoic acid)-Cys-(6-aminohexanoic acid)-Gly-Gly-Ser-Gly-Gly-Ser-Gly-Gly) may be also further bound to N-terminal Tyr of the Peptide 5-2-4 or 5-2-4C (hereinafter also referred to as 'Peptide FITC-5-2-4' or 'Peptide FITC-5-2-4C'). Likewise, an amide group may also be bound to C-terminal Cys of the peptide FITC-5-2-4C.

Furthermore, in order to increase blood-brain barrier (BBB) penetration and cell penetrability of the peptide, a dNP2 peptide sequence (KIKKVKKKGRKGSKIKKVKK-KGRKGG; Lim et al., Nat Commun (2015) 6, 8244) having such functions may also be bound to the N-terminal Tyr of the Peptide 5-2-4 (hereinafter also referred to as 'Peptide 5-2-4D'). Likewise, acetyl and amide groups may also be bound to N-terminal Lys and C-terminal Arg of the Peptide 5-2-4D, respectively.

To facilitate the analysis of binding between the Peptide 5-2-4C and a transcription factor CP2c, biotin-tagged Lys may also be bound to ε-NH$_2$ of the C-terminal Cys of the Peptide 5-2-4C (hereinafter also referred to as 'Peptide 5-2-4CB'). Likewise, acetyl and amide groups may also be bound to N-terminal Tyr and C-terminal Cys of the Peptide 5-2-4CB, respectively.

Meanwhile, there are provided a pharmaceutical composition, a health functional food composition, and a functional cosmetic composition for preventing and treating cancer including the peptide set forth in SEQ ID NO: 1 as an active ingredient.

In the present invention, the term "treatment" refers to all actions in which the symptoms of cancer have been improved or changed in an advantageous way by the administration of the peptide of the present invention or the pharmaceutical composition including the peptide.

In the present invention, the term "administration" refers to the introduction of a certain substance, that is, the peptide derivatives of the present invention or the pharmaceutical composition including the peptide derivatives, into a subject by any suitable method. The peptide derivatives of the present invention or the pharmaceutical composition including the peptide derivatives may be administered via any common routes of administration as long as the drugs can reach a desired tissue.

In the present invention, the expression "containing as an active ingredient" refers to the presence of an amount sufficient to treat a disease in a reasonable beneficial/risk ratio applicable to any medical treatment. In this case, an effective dosage level of the pharmaceutical composition may be determined depending on the factors including the type and severity of a patient's disease, the activity of a drug, the patient's sensitivity to the drug, the administration time, the route of administration, the excretion rate, the duration of treatment, drugs used in combination with the composition, and other factors known in the medical field.

Therefore, the pharmaceutical composition according to the present invention may include one or more pharmaceutically acceptable carriers so long as it contains the peptide according to the present invention as an active ingredient.

The peptide according to the present invention may be included as the active ingredient of the health functional food composition. In this case, the food composition according to the present invention may be mixed with active ingredients known to have anticancer activity. In this case, the resulting mixture may be prepared in the form of a composition. Also, the food composition of the present invention may further include a sitologically acceptable food supplement additive. The health functional food composition of the present invention includes compositions for all types of foods, such as functional foods, nutritional supplements, health foods, and food additives.

Further, the peptide according to the present invention may also be included as the active ingredient in the functional cosmetic composition. In this case, the peptide of the present invention may be used in separate cosmetics or used in combination with other functional cosmetics. In the present invention, the term "functional cosmetic composition" refers to a composition having an effective healing effect on various skin diseases when the composition includes the peptide according to the present invention. In this case, the functional cosmetic composition may be administered in the minimal amount that can exhibit the maximum effect without causing any side effects in consideration of all the aforementioned factors.

The functional cosmetic composition including the peptide according to the present invention may be prepared into any form of formulation commonly prepared in the related art.

Mode for Invention

The present invention will be described in further detail with reference to the following examples. However, it should be understood that these examples are merely provided to assist in understanding the invention, and are not intended to limit the scope of the present invention.

EXAMPLE 1

Inhibition of CP2c-DNA Binding by Peptide 5

EXAMPLE 1.1

To identify peptide motifs interacting with a murine CP2c protein, five binding motifs (Peptide 5, Peptide 8, Peptide 13, Peptide 21, and Peptide 31) were identified using a phage display method disclosed in preceding research conducted by the present inventors.

EXAMPLE 1.2

To analyze whether the five peptides identified in Example 1.1 bind to CP2c in cells to affect the ability of CP2c to bind to DNA, a DNA immunoprecipitation (DIP) assay was performed as disclosed in another preceding study conducted by the present inventors.

In summary, the differentiation of a murine erythroid leukemia (MEL) cell line was induced by treating the MEL cell line with 5 mM hexamethylene bisacetamide (HMBA), and a cellular nuclear extract was then separated on day 2 after the differentiation. For the separation of the nuclear extract, first, 1×10$^6$ cells of the cell line were harvested, and then washed with PBS. Thereafter, 200 µL of nuclear extraction buffer A (10 mM HEPES, 10 mM KCl, 0.1 mM EDTA, 0.1 mM EGTA, 0.5 mM phenylmethylsulfonyl fluoride, a protease inhibitor cocktail (Roche)) was added, and the resulting mixture was then reacted at 4° C. for 15 minutes. When the reaction was completed, 0.6% NP-40 was added to the resulting reaction mixture. Then, the resulting turbid solution was centrifuged, and the supernatant was discarded. 50 µL of nuclear extraction buffer C (20 mM HEPES, 400 mM NaCl, 1 mM EDTA, 1 mM EGTA, 1 mM phenylmethylsulfonyl fluoride, and a protease inhibitor cocktail (Roche)) was added to the pellet remaining after the centrifugation. The pellet was detached by tapping at 4° C.

for 5 to 10 minutes, and then centrifuged to obtain a supernatant, which was then used for subsequent experiments.

Next, 5 μg of the separated nuclear extract and an [α-32p] dCTP-labeled DNA probe (a sequence corresponding to the CP2c consensus binding site present in a murine α-globin promoter and composed of amino acids between −156 and −124 in the initiation codon of an α-globin gene, see the paper of Kim et al. for more details on the sequence) were reacted with a binding buffer (4% glycerol, 10 mM Tris-HCl, 1 mM DTT, 1 mM EDTA, and 0.1% NP-40) for 15 minutes, and gradually increasing amounts (0.2, 0.5, and 1 μg) of the identified CP2c binding peptides (Peptide 5, Peptide 8, Peptide 13, Peptide 21, and Peptide 31) were added thereto. Thereafter, the reaction was continued at room temperature for another 15 minutes. Thereafter, 20 μL of a 50% protein G-agarose bead suspension was added to each reaction mixture. The resulting mixture was reacted at 4° C. for an hour to remove non-specific binding. 2 μg of an anti-CP2c antibody (Cosmo Genetech) was added thereto, and the resulting mixture was reacted at 4° C. for 10 hours. 20 μL of a 50% protein G-agarose bead suspension was added to the reaction product bound to the CP2c antibody. The reaction was carried out at 4° C. for 2 hours. Subsequently, the reaction mixture was washed three times with a cell lysis buffer (50 mM Tris-HCl, 150 mM NaCl, 1 mM EDTA, and 1 mM phenylmethylsulfonyl fluoride). An elution buffer (50 mM Tris-HCl, 10 mM EDTA, and 1% sodium dodecyl sulfate) was added to the CP2c-bound DNA probe, and the resulting mixture was then reacted at 65° C. for an hour. The CP2c protein was removed from the DNA probe and a residual amount of the DNA probe was measured using a scintillation counter.

In order to investigate which peptide sequence fragments of the full-length CP2c sequence composed of a total of 6 regions interact with the CP2c regions, the full-length CP2c sequence and sequences of various CP2c mutants, in which the N- and C-termini of the CP2c sequence are depleted, are schematically shown in FIG. 1. Also, FIG. 2 shows the binding affinities of the DNA-CP2c complexes measured by performing a DIP assay for the five identified CP2c-binding peptides (Peptide 5, Peptide 8, Peptide 13, Peptide 21, and Peptide 31). Referring to FIGS. 1 and 2, it can be seen that Peptide 5 specifically inhibited the CP2c-DNA binding in a concentration-dependent manner.

EXAMPLE 2

Inhibition of CP2c-DNA Binding by Peptides 5-1 and 5-2

CP2c-binding Peptide 5 having a sequence composed of 12 amino acids was equally cleaved into two peptides: Peptides 5-1 and 5-2, each of which was composed of 6 amino acids. Thereafter, an inhibitory effect of Peptides 5-1 and 5-2 on the ability of CP2c to bind to DNA was analyzed by the same method as described in Example 1.

FIG. 3 shows the binding affinities of DNA-CP2c complexes measured by performing a DIP assay for Peptide 5, Peptide 8, Peptide 5-1, and Peptide 5-2. Referring to FIG. 3, it can be seen that Peptide 8 and Peptide 5-1 poorly inhibited the ability of CP2c to bind to DNA, but Peptide 5-2 specifically inhibited the binding between CP2c and DNA to almost the same extent as Peptide 5.

EXAMPLE 3

Construction of Modified Peptides from Peptide 5-2

To analyze whether the Peptide 5-2 composed of six amino acids prepared in Example 2 is composed of the amino acids having an optimized anticancer effect and a peptide composed of a lesser number of amino acids has the same effect, Peptides 5-2-51 and 5-2-52 in which one of both terminal amino acids was removed from Peptide 5-2, Peptide 5-2-4 in which both terminal amino acids were removed one by one, and Peptides 5-2-31 and 5-2-32 in which one of both terminal amino acids was removed from Peptide 5-2-4 were constructed. Amino acid sequences of the constructed peptides are as follows.

| | |
|---|---|
| 5-2-51: | $NH_2$-NYPQR-COOH |
| 5-2-52: | $NH_2$-YPQRP-COOH |
| 5-2-4: | $NH_2$-YPQR-COOH |
| 5-2-31: | $NH_2$-YPQ-COOH |
| 5-2-32: | $NH_2$-PQR-COOH |

Also, the aforementioned CP2c-binding peptides are very unstable, and thus tend to be easily decomposed in a culture fluid when cells are treated with the peptides during the culture, and also have limitations in performing an in vivo experiment because the CP2c-binding peptides do not pass through cell membranes when the cells are treated with the peptides. Therefore, the CP2c-binding peptides need to be subjected to modifications made in order to enhance the stability and the cell penetrability of the peptide. To compensate for these problems, peptide sequences in which acetyl and amide groups were attached to the N-terminus and C-terminus of the peptide as a modification made in order to enhance the stability of the peptide, respectively, and an iRGD peptide sequence (CRGDKGPDC) binding to a neuropilin 1 receptor was attached as a modification made in order to enhance the cell penetrability of the peptide were constructed. Amino acid sequences of the constructed peptides were as follows.

| | |
|---|---|
| 5-2-51C: | Ac-NYPQRcrgdkgpdc-amide |
| 5-2-52C: | Ac-YPQRPcrgdkgpdc-amide |
| 5-2-4C: | Ac-YPQRcrgdkgpdc-amide |
| 5-2-31C: | Ac-YPQcrgdkgpdc-amide |
| 5-2-32C: | Ac-PQRcrgdkgpdc-amide |

EXAMPLE 4

Analysis of Cell Growth Inhibition and Apoptosis-inducing Effects of Peptides

An embryonic kidney cell line (293T), a breast cancer cell line (MDA-MB-231), and colon cancer cell lines (HCT116 and HT29) were inoculated in a 96-well plate at a density of 3,000 cells/well, and 50 μL of a culture fluid was added thereto. The resulting mixture was cultured for an hour under 37° C./5% $CO_2$ conditions. Each of the peptides prepared in Example 3 was added at an increasing concentration of 0.05, 1, 2, 3 and 10 μM to the well plate inoculated with each of the cell lines, and the resulting mixture was cultured for 0, 24, 48, 72 and 96 hours under 37° C./5% $CO_2$ conditions. When the culture was completed, the cells were observed and their morphological changes were imaged using an inverted phase contrast microscope.

FIGS. 4A and 4B graphically show the growth inhibition and apoptosis-inducing effects of the untreated control and the Peptides 5-2C, 5-2-51C, 5-2-52C and 5-2-4C on the breast cancer cell line (4A) and the embryonic kidney cell line (4B). Referring to FIGS. 4A and 4B, it can be seen that Peptides 5-2C, 5-2-51C, 5-2-52C and 5-2-4C exhibited growth inhibition and apoptosis-inducing effects on the breast cancer cell line and the embryonic kidney cell line in a concentration-dependent manner, compared to the untreated control.

Also, FIGS. 5A and 5B graphically show the growth inhibition and apoptosis-inducing effects of the untreated control and the Peptides 5-2C, 5-2-51C, 5-2-52C and 5-2-4C on the two colon cancer cell lines (HCT116 and HT29). Referring to FIGS. 5A and 5B, it can also be seen that Peptides 5-2C, 5-2-51C, 5-2-52C and 5-2-4C exhibited growth inhibition and apoptosis-inducing effects on the colon cancer cell lines in a concentration-dependent manner, compared to the untreated control.

In addition, FIGS. 6A to 6C include an image (6A) of the cells, a graph (6B) for cell growth inhibition by means of an MTT assay for calculating $IC_{50}$ values, and an image (6C) of 96-well plates for MTT assay at the elapsed time of 96 hours after the embryonic kidney cell line (293T), the breast cancer cell line (MDA-MB-231), and the colon cancer cell lines (HCT116 and HT29) are treated with the untreated control, and the Peptides 5-2C, 5-2-51C, 5-2-52C and 5-2-4C for 48 hours. Referring to FIGS. 6A to 6C, it can be seen that Peptides 5-2C, 5-2-51C, 5-2-52C and 5-2-4C exhibited superior growth inhibition and apoptosis-inducing effects, compared to the untreated control.

Meanwhile, FIG. 7A is a diagram showing growth inhibition and apoptosis-inducing effects of Peptides 5-2C, 5-2-4C, iRGD, 5-2-31C and 5-2-32C on the breast cancer cell line (MDA-MB-231). Referring to FIG. 7A, it can be seen that the iRGD peptide and Peptides 5-2-31C and 5-2-32C composed of three amino acids exhibited no growth inhibition and apoptosis-inducing effects at all. Also, these facts may be proven from the image of cells as shown in FIG. 7B, the image of 96-well plates for MTT assay at the elapsed time of 96 hours as shown in FIG. 7C, and the graph for cell growth inhibition by means of an MTT assay for calculating $IC_{50}$ values as shown in FIG. 7D.

Therefore, it can be seen that the peptide having a sequence with a minimum length of amino acids derived from Peptide 5-2C to exhibit cell growth inhibition and apoptosis-inducing effects was the peptide of SEQ ID NO: 1 having a sequence composed of four amino acids.

Further, experiments were also conducted to check whether the modified peptides in which each of the amino acids constituting the peptide set forth in SEQ ID NO: 1 was modified exhibit the same cell growth inhibition and apoptosis-inducing effects as the peptide of SEQ ID NO: 1. Specifically, because the first amino acid of the sequence of four amino acids (YPQR) constituting the peptide of SEQ ID NO: 1 was tyrosine (Y) capable of being phosphorylated, peptides (5-2-4/1F, 5-2-4/1S, and 5-2-4/1T) in which tyrosine (Y) was substituted with other phosphorylatable amino acids (S and T) and phenylalanine (F) having properties similar to tyrosine were constructed. Thereafter, experiments were conducted on the Peptides 5-2-4/1F, 5-2-4/1S, and 5-2-4/1T. For the same reasons, peptides (5-2-4/2G, 5-2-4/3N, 5-2-4/4K) in which the second amino acid (P), the third amino acid (Q), and the fourth amino acid (R) were substituted with G, N and K, respectively, were also constructed. In order to enhance the stability and cell penetrability of the peptide, peptides whose N- and C-termini were modified and which had an iRGD amino acid sequence bound thereto were also constructed (5-2-4C/1F, 5-2-4C/1S, 5-2-4C/1T, 5-2-4C/2G, 5-2-4C/3N, 5-2-4C/4K). The constructed peptides were as follows.

```
5-2-4C/1F:    Ac-FPQRcrgdkgpdc-amide
5-2-4C/1S:    Ac-SPQRcrgdkgpdc-amide
5-2-4C/1T:    Ac-TPQRcrgdkgpdc-amide
5-2-4C/2G:    Ac-YGQRcrgdkgpdc-amide
5-2-4C/3N:    Ac-YPNRcrgdkgpdc-amide
5-2-4C/4K:    Ac-YPQKcrgdkgpdc-amide
```

The peptides were used to analyze effects on cell growth inhibition and apoptosis in the liver cancer cell line (Hep3B). The results are shown in FIGS. 8A to 8D. FIGS. 8A and 8B show respective images of the 96-well plates for MTT assay stained with a cell counting kit (CCK) and Crystal Violet (CV) at the elapsed time of 96 hours, and FIGS. 8C and 8D graphically show the growth inhibition and apoptosis-inducing effects of the respective peptides at different concentrations. Referring to FIGS. 8A to 8D, it can be seen that, when one of the four amino acids constituting the peptide of SEQ ID NO: 1 was modified with another amino acid, the peptides exhibited no cell growth inhibition and apoptosis-inducing effects. Therefore, it can be seen that the peptide of SEQ ID NO: 1 according to the present invention is a peptide having a sequence composed of an optimized number of amino acids to have anticancer activity.

In preceding research conducted by the present inventors, Peptide 5-2 induced the superior cancer cell-specific growth inhibition and apoptosis in normal cell lines and stem cell lines as well as cancer cell lines of various origins. Therefore, to analyze whether the minimal/optimized Peptide 5-2-4 according to the present invention exhibited the same effects in the cancer cell lines of various origins and the normal cell/stem cell lines, first, a Hep3B liver cancer cell line was treated once with Peptide 5-2-4, and a change in $IC_{50}$ values observed for 3 days was then compared to that of the 5-2C-treated group. As a result, Peptide 5-2-4C had an $IC_{50}$ value steadily decreasing over 3 days, a level of which was highly similar to that of Peptide 5-2C (see FIG. 9).

In the analysis of growth inhibition and apoptosis in leukemia cells (FIGS. 10A and 10B); breast cancer cells (FIGS. 11A and 11B); colon cancer cells (FIGS. 12A and 12B); and liver cancer cells and kidney-derived cells (FIGS. 13A and 13B), Peptide 5-2-4C exhibited a tendency very similar to Peptide 5-2C. These results can be confirmed from the image of the cells as shown in FIG. 14 and the image of well plates for MTT assay after 96 hours have elapsed. Referring to FIG. 16, it can also be seen that Peptide 5-2-4C tended to have an $IC_{50}$ value at 48 hours very similar to that of Peptide 5-2C.

INDUSTRIAL APPLICABILITY

The Peptide 5-2-4C according to the present invention can pass through the cell membranes of cancer cells to specifically bind to CP2c due to very high stability when the cancer cells are treated with the Peptide 5-2-4C. Therefore, the Peptide 5-2-4C of the present invention can inhibit the activity of CP2c, and thus can be effectively used to treat cancer by inducing cell growth inhibition and apoptosis in various CP2c-mediated cancer cells.

The invention claimed is:

1. A peptide comprising the following SEQ ID NOs: 1 and 2:

<SEQ ID NO: 1>
Tyr-Pro-Gln-Arg

<SEQ ID NO: 2>
Cys-Arg-Gly-Asp-Lys-Gly-Pro-Asp-Cys wherein the peptide set forth in SEQ ID NO: 2 is bound to the C-terminal Arg of the peptide set forth in SEQ ID NO: 1.

2. The peptide of claim 1, further comprising an acetyl and an amide group bound to the N-terminal Tyr of the peptide set forth in SEQ ID NO: 1 and C-terminal Cys of the peptide set forth in SEQ ID NO: 2, respectively.

3. The peptide of claim 1, further comprising a peptide set forth in the following SEQ ID NO: 3 bound to the N-terminal Tyr of the peptide set forth in SEQ ID NO: 1, and fluorescein isothiocyanate (FITC) bound to N-terminal Lys of the peptide set forth in the following SEQ ID NO: 3:

<SEQ ID NO: 3>
Lys-Cys-Lys-Gly-Gly-Ser-Gly-Gly-Ser (provided that each of Lys 1 and 3 residues of the sequence is 6-aminohexanoic acid.).

4. The peptide of claim 3, further comprising an amide group bound to the C-terminal Cys of the peptide set forth in SEQ ID NO: 2.

5. A peptide comprising the following SEQ ID NOs: 1 and 4:

<SEQ ID NO: 1>
Tyr-Pro-Gln-Arg

<SEQ ID NO: 4>
Arg-Gly-Asp.

wherein the peptide set forth in SEQ ID NO: 4 is bound to the C-terminal Arg of the peptide set forth in SEQ ID NO: 1.

6. The peptide of claim 5, further comprising an acetyl and an amide group bound to the N-terminal Tyr of the peptide set forth in SEQ ID NO: 1 and C-terminal Asp of the peptide set forth in SEQ ID NO: 4, respectively.

7. The peptide of claim 5, wherein a cyclic peptide is formed via a direct peptide bond between the amino group of the N-terminal Tyr of the peptide set forth in SEQ ID NO: 1 and the carboxyl group of the C-terminal Asp of the peptide set forth in SEQ ID NO: 4.

8. A peptide comprising the following SEQ ID NOs: 1 and 5:

<SEQ ID NO: 1>
Tyr-Pro-Gln-Arg

<SEQ ID NO: 5>
Lys-Ile-Lys-Lys-Val-Lys-Lys-Lys-Gly-Arg-Lys-Gly-
Ser-Lys-Ile-Lys-Lys-Val-Lys-Lys-Lys-Gly-Arg-Lys-
Gly-Gly wherein the peptide set forth in SEQ ID NO: 5 is bound to the N-terminal Tyr of the peptide set forth in SEQ ID NO: 1.

9. The peptide of claim 8, further comprising an acetyl and an amide group bound to N-terminal Lys of the peptide set forth in SEQ ID NO: 5 and the C-terminal Arg of the peptide set forth in SEQ ID NO: 1, respectively.

10. The peptide of claim 1, further comprising a biotin-labeled Lys bound to ε-$NH_2$ of the C-terminal Cys of the peptide set forth in SEQ ID NO: 2.

11. The peptide of claim 10, further comprising an acetyl and an amide group bound to the N-terminal Tyr of the peptide set forth in SEQ ID NO: 1 and the biotin-labeled C-terminal Lys bound to the ε-$NH_2$ of the C-terminal Cys of the peptide set forth in SEQ ID NO: 2, respectively.

12. A pharmaceutical composition for preventing and treating cancer comprising the peptide as in claims 1, 5 or 8 as an active ingredient.

13. A health functional food composition for preventing and treating cancer comprising the peptide as in claims 1, 5 or 8 as an active ingredient.

14. A functional cosmetic composition comprising the peptide as in claim 1, 5 or 8 as an active ingredient.

* * * * *

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: artificially synthesized peptide

<400> SEQUENCE: 1

Tyr Pro Gln Arg
1

<210> SEQ ID NO 2
<211> LENGTH: 9
<212> TYPE: PRT
<213> ORGANISM: Artificial Sequence
<220> FEATURE:
<223> OTHER INFORMATION: artificially synthesized peptide

<400> SEQUENCE: 2

Cys Arg Gly Asp Lys Gly Pro Asp Cys
1               5

<210> SEQ ID NO 3
<211> LENGTH: 9
<212> TYPE: PRT
<213> ORGANISM: Artificial Sequence
<220> FEATURE:
<223> OTHER INFORMATION: artificially synthesized peptide
<220> FEATURE:
<221> NAME/KEY: MOD_RES
<222> LOCATION: (1)..(3)
<223> OTHER INFORMATION: No. 1 Lys and No. 3 Lys are 6-aminohexanoic
      acids

<400> SEQUENCE: 3

Lys Cys Lys Gly Gly Ser Gly Gly Ser
1               5

<210> SEQ ID NO 4
<211> LENGTH: 3
<212> TYPE: PRT
<213> ORGANISM: Artificial Sequence
<220> FEATURE:
<223> OTHER INFORMATION: artificially synthesized peptide

<400> SEQUENCE: 4

Arg Gly Asp
1

<210> SEQ ID NO 5
<211> LENGTH: 26
<212> TYPE: PRT
<213> ORGANISM: Artificial Sequence
<220> FEATURE:
<223> OTHER INFORMATION: artificially synthesized peptide

<400> SEQUENCE: 5

Lys Ile Lys Lys Val Lys Lys Lys Gly Arg Lys Gly Ser Lys Ile Lys
1               5                   10                  15

Lys Val Lys Lys Lys Gly Arg Lys Gly Gly
            20                  25